US012569478B2

(12) United States Patent
Li et al.

(10) Patent No.: US 12,569,478 B2
(45) Date of Patent: Mar. 10, 2026

(54) SEQUESTRATION COMPOUNDS FOR TREATMENT OF SUBSTANCE USE DISORDER AND USES THEREOF

(71) Applicant: Clear Scientific, Inc., Cambridge, MA (US)

(72) Inventors: Xinhua Li, Newton, MA (US); Mitchell Zakin, Andover, MA (US); Chandrashekar Shetty, Brookline, MA (US); Piercen Oliver, Malden, MA (US); Daniel Wallach, Melrose, MA (US)

(73) Assignee: Clear Scientific, Inc., Cambridge, MA (US)

( * ) Notice: Subject to any disclaimer, the term of this patent is extended or adjusted under 35 U.S.C. 154(b) by 1066 days.

(21) Appl. No.: 17/669,122

(22) Filed: Feb. 10, 2022

(65) Prior Publication Data

US 2022/0313687 A1 Oct. 6, 2022

Related U.S. Application Data

(63) Continuation of application No. PCT/US2022/014695, filed on Feb. 1, 2022.

(60) Provisional application No. 63/144,441, filed on Feb. 1, 2021.

(51) Int. Cl.
*A61K 31/485* (2006.01)
*A61K 31/551* (2006.01)
*A61P 25/36* (2006.01)

(52) U.S. Cl.
CPC .......... *A61K 31/485* (2013.01); *A61K 31/551* (2013.01); *A61P 25/36* (2018.01)

(58) Field of Classification Search
CPC ...... A61K 31/485; A61K 31/551; A61P 25/36
See application file for complete search history.

(56) References Cited

U.S. PATENT DOCUMENTS

2006/0240085 A1 10/2006 Reidenberg et al.
2013/0345202 A1 12/2013 Amselem
2017/0172522 A1* 6/2017 Insler .................... A61B 5/4845
2018/0161320 A1* 6/2018 Wyse .................... A61K 9/0043

FOREIGN PATENT DOCUMENTS

WO WO-2020041006 A2 2/2020
WO WO-2020206391 A1 10/2020
WO WO-2022165407 A1 8/2022

OTHER PUBLICATIONS

Chou, T. C. Cancer research 70.2 (2010): 440-446. (Year: 2010).*
Berenbaum, M. C. Clin. Exp. Immunol., 1977, 28, 1-18. (Year: 1977).*
International Search Report and Written Opinion for PCT/US/2022/14695 issued Jun. 3, 2022.
International Preliminary Report on Patentability issued in PCT/US2022/014695, dated Jul. 31, 2023.
Thevathasan, et al., Calabadion 1 selectively reverses respiratory and central nervous system effects of fentanyl in a rat model, British Journal of Anesthesia, 125(1):E140-E147, (2020).
Dahan, et al., From breathtaking to encapsulation: a novel approach to reverse respiratory depression from opioid overdosing, British Journal of Anaesthesia, 125 (1): e16-e17 (2020).
France, Charles P. et al. Countermeasures for Preventing and Treating Opioid Overdose. Clinical pharmacology and therapeutics 109(3):578-590 (2021) Published online Nov. 29, 2020.
Ganapati, Shweta. et al. Molecular Containers Bind Drugs of Abuse in Vitro and Reverse the Hyperlocomotive Effect of Methamphetamine in Rats. Chembiochem 18(16):1583-1588 (2017).
Mueller, Shane R. et al. A Review of Opioid Overdose Prevention and Naloxone Prescribing: Implications for Translating Community Programming Into Clinical Practice. Substance abuse 36(2):240-253 (2015).
Yeung, David T. et al. National Institutes of Health (NIH) Executive Meeting Summary: Developing Medical Countermeasures to Rescue Opioid-Induced Respiratory Depression (a Trans-Agency Scientific Meeting)—Aug. 6/7, 2019. Journal of medical toxicology 16(1):87-105 (2020). Published online Dec. 18, 2019.
Deng, Chun-Lin et al. “Supramolecular Hosts as In Vivo Sequestration Agents for Pharmaceuticals and Toxins” Chem soc Rev (2020) 49(21): 7516-7532.
International Search Report and Written Opinion for PCT/US2022/014695 dated Mar. 6, 2022.
Thevathasan, et al., Calabadion 1 selectively reverses respiratory and central nervous system effects of fentanyl in a rat model, A Novel Strategy to Selectively Reverse Respiratory and Central Nervous System effects of Fentanyl, British Journal of Anaesthesia, 125(1):E140-E147, (2020), Supplemental Information.

* cited by examiner

*Primary Examiner* — Kamal A Saeed
*Assistant Examiner* — Quincy McKoy
(74) *Attorney, Agent, or Firm* — WILSON SONSINI GOODRICH & ROSATI

(57) ABSTRACT

Described herein are i) sequestering agents and ii) central nervous system (CNS) active agents for the treatment of intoxication due to toxic agents such as drugs of abuse, and associated symptoms. Also disclosed herein, are a cucurbituril and naloxone for use in the treatment of opioid overdoses through sequestering and excretion of the bound molecule of interest through the urine. Also provided herein, are kits and methods of treatment of the disclosure.

30 Claims, 4 Drawing Sheets

SEQUESTRATION COMPOUNDS FOR TREATMENT OF SUBSTANCE USE DISORDER AND USES THEREOF

CROSS-REFERENCE

This application is a continuation of PCT application Serial Number PCT/US2022/014695, filed Feb. 1, 2022, which claims the benefit of U.S. Provisional Application No. 63/144,441, filed Feb. 1, 2021, which applications are incorporated herein by reference in their entirety.

STATEMENT AS TO FEDERALLY SPONSORED RESEARCH

This disclosure was made with government support through a research collaboration between the NIH Office of the Director (OD) and the U.S. Army Medical Research Institute of Chemical Defense under the oversight of the Chemical Countermeasures Research Program (CCRP) within the Office of Biodefense Research (OBRS) at the National Institute of Allergy and Infectious Diseases (NIAID/NIH). The government has certain rights in the disclosure.

BACKGROUND OF THE DISCLOSURE

Drug overdose or intoxication is a major social issue that affects all aspects of society. Drug overdose can be due to prescribed for illegal substances such as opioids (e.g., fentanyl and its derivatives), stimulants (e.g., methamphetamine) and other substances. Drug overdose or intoxication of stimulants such as methamphetamine, and stimulants and opioids) is also an issue. Stimulant and stimulant/opioid overdoses can also be due to prescribed, diverted or illegal substances.

There remains a need for methods and compositions for the treatment of patients who have been subjected to drug overdose or drug intoxication, the treatment of patients who have been subjected to opioid overdose, the treatment of patients who have been subjected to stimulant overdose, the treatment of patients who have been subjected to combined stimulant and opioid overdose, whether by accidental drug overdose or other means.

SUMMARY OF THE DISCLOSURE

The present disclosure provides compositions and methods for addressing these and other circumstances wherein it is desirable to reverse the effect of one or more drugs, including but not necessarily limited to toxic agents such as drugs of abuse.

In some embodiments, the disclosure provides a pharmaceutical combination for use in treating intoxication, overdose, or a symptom thereof due to at least one toxic agent in a human comprising: i) a sequestration agent or a pharmaceutically acceptable salt thereof in an amount sufficient to sequester the at least one toxic agent; and ii) a central nervous system (CNS) active agent or a pharmaceutically acceptable salt thereof; wherein the sequestration agent is a cucurbituril, a pillararene, a cyclodextrin or a calixarene; and wherein the sequestration agent and the CNS active agent are administered or are suitable for administration simultaneously, or sequentially less than about 5 minutes apart.

In some embodiments, the disclosure provides a pharmaceutical combination for use in treating intoxication, overdose or a symptom thereof due to at least one toxic agent selected from the group consisting of a stimulant, a nerve agent, an allergen, and a metabolically or digestion derived toxicant in a human, comprising: i) a sequestration agent or a pharmaceutically acceptable salt thereof in an amount sufficient to sequester the at least one toxic agent; and ii) a central nervous system (CNS) active agent or a pharmaceutically acceptable salt thereof; wherein the sequestration agent is a cucurbituril, a pillararene, a cyclodextrin or a calixarene.

In some embodiments, the disclosure provides a pharmaceutical combination for use in treating a suspected overdose or symptom thereof in a subject comprising: i) a sequestration agent or a pharmaceutically acceptable salt thereof in an amount sufficient to sequester at least one toxic agent; and ii) a central nervous system (CNS) active agent or a pharmaceutically acceptable salt thereof; wherein the sequestration agent is a cucurbituril, a pillararene, a cyclodextrin or a calixarene; and wherein the subject has a suspected overdose from a plurality of toxic agents. In some embodiments, the plurality of toxic agents comprises at least 1, at least 2, at least 3, at least 4 toxic agents.

In some embodiments, the disclosure provides a pharmaceutical composition comprising: i) a sequestration agent or a pharmaceutically acceptable salt thereof in an amount sufficient to sequester at least one toxic agent; ii) a central nervous system (CNS) active agent or a pharmaceutically acceptable salt thereof; and iii) a pharmaceutically acceptable excipient; wherein the sequestration agent is a cucurbituril, a pillararene, a cyclodextrin or a calixarene.

In some embodiments, the disclosure provides a method of treating intoxication, overdose, or a symptom thereof due to at least one toxic agent in a human comprising administering a therapeutically effective amount of: i) a sequestration agent or a pharmaceutically acceptable salt thereof in an amount sufficient to sequester the at least one toxic agent; and ii) a central nervous system (CNS) active agent or a pharmaceutically acceptable salt thereof; wherein the sequestration agent is a cucurbituril, a pillararene, a cyclodextrin or a calixarene; and wherein the sequestration agent and the CNS active agent are administered simultaneously, or sequentially less than about 5 minutes apart.

In some embodiments, the present disclosure provides a method of treating an intoxication, overdose or a symptom thereof due to a stimulant, a nerve agent, an allergen, and a metabolically or digestion derived toxicant in a human, the method comprising: co-administering a therapeutically effective amount of a sequestration agent or a pharmaceutically acceptable salt thereof, with a therapeutically effective amount of a central nervous system (CNS) active agent or a pharmaceutically acceptable salt thereof, wherein the co-administration is effective to treat the stimulant, nerve agent, allergen or metabolically and digestion derived toxicant overdose or symptom thereof in the human in need thereof.

In some embodiments, the present disclosure provides a method of treating a suspected overdose or symptom thereof in a subject, comprising coadministering a therapeutically effective amount of a sequestration agent or a pharmaceutically acceptable salt thereof, with a therapeutically effective amount of a central nervous system (CNS) active agent or a pharmaceutically acceptable salt thereof, wherein the subject has a suspected overdose from a plurality of toxic agents. In some embodiments, the plurality of toxic agents comprises at least 1, at least 2, at least 3, at least 4 toxic agents.

In some embodiments, the sequestration agent and CNS active agent are in the same formulation. In some embodiments, the sequestration agent and CNS active agent are in different formulations. The formulation may further comprise a pharmaceutically-acceptable excipient.

In some embodiments, the sequestration agent and the CNS active agent are administered simultaneously. In accordance with this embodiment, the sequestration agent and the CNS active agent may be present in the same formulation (i.e., the sequestration agent and the CNS active agent are co-formulated. Alternative, the sequestration agent and the CNS active agent may be present in different formulations that are co-administered at the same time or close in time.

In some embodiments, the sequestration agent and the CNS active agent are administered sequentially, preferably less than about 5 minutes apart, for example less than about 4 minutes apart, less than 3 minutes apart, less than 2 minutes apart, less than one minute apart, and the like. For example, in one embodiment, the CNS active agent is administered first, and the sequestration agent is administered less than about 4 minutes, about 3 minutes, about 2 minutes, or about 1 minute after the CNS active agent. In another embodiment, the sequestration agent is administered first, and the CNS active agent is administered less than about 4 minutes, about 3 minutes, about 2 minutes, or about 1 minute after the sequestration agent.

chlordiazepoxide, clorazepate, halazepam, oxazepam, prazepam, and quazepam, or a pharmaceutically acceptable salt thereof.

In some embodiments, the CNS active agent is an antihistamine. In some embodiments, the CNS active agent is an antihistamine selected form the group consisting of: cetirizine, diphenhydramine, fexofenadine, loratadine, desloratadine, clemastine, chlorpheniramine, levocetirizine, cyproheptadine, carbinoxamine, emedastine, levocabastine, or pharmaceutically acceptable salts thereof.

In some embodiments, the CNS active agent is ketamine or a pharmaceutically acceptable salt thereof.

In some embodiments, the CNS active agent is atropine or a pharmaceutically acceptable salt thereof. In some embodiments, the CNS active agent is scopolamine or a pharmaceutically acceptable salt thereof.

In some embodiments, the sequestration agent is a cucurbituril. In some embodiments, the sequestration agent is an acyclic cucurbituril. In some embodiments, the sequestration agent is a cyclic cucurbituril. In some embodiments, the sequestration agent is a pillararene. In some embodiments, the sequestration agent is a cyclodextrin. In some embodiments, the sequestration agent is a calixarene. In some embodiments, the sequestration agent is Compound A or any derivatives thereof, wherein Compound A comprises the following structure:

Compound A

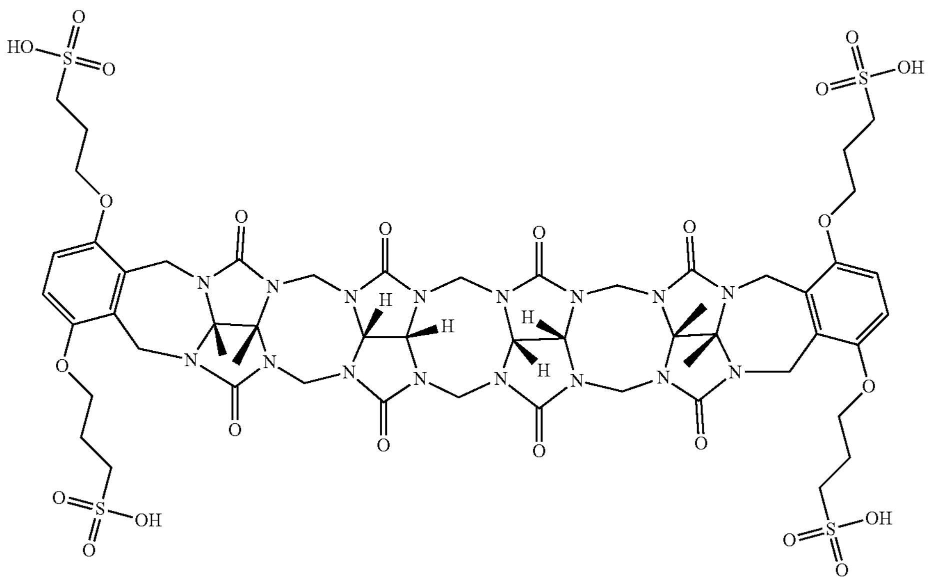

In some embodiments, the CNS active agent is an opioid receptor antagonist. In some embodiments, the CNS active agent is a mu opioid receptor antagonist. In some embodiments, the CNS active agent is selected form the group consisting of: naloxone, pentazocine, nalbuphine, diprenorphine, methylnaltrexone, naloxegol, alvimopan, naltrexone, nalmefene, buprenorphine, or a pharmaceutically acceptable salt thereof. In some embodiments, the CNS active agent is naloxone.

In some embodiments, the CNS active agent is a benzodiazepine. In some embodiments, the CNS active agent is a benzodiazepine selected from the group consisting of: lorazepam, Klonopin, clonazepam, diazepam, alprazolam, In some embodiments, the toxic agent is a drug of abuse.

In some embodiments, the toxic agent is an opioid. In some embodiments, the sequestration agent binds to the opioid with a $K_a$ of at least about $1\times10^3 M^{-1}$, $1\times10^4 M^{-1}$, $1\times10^5\ M^{-1}$, $1\times10^6 M^{-1}$, $1\times10^7 M^{-1}$, $1\times10^8\ M^{-1}$, or $1\times10^9\ M^{-1}$. In some embodiments, the opioid is selected a group consisting of fentanyl, fentanyl analogs, carfentanil, sufentanil, acetylfentanyl, alfentanil, heroin, morphine, oxycodone, codeine, hydrocodone, oxymorphone, and any pharmaceutically acceptable salts, and any combinations thereof.

In some embodiments, the toxic agent is selected from the group consisting of a stimulant, a nerve agent, an allergen, and a metabolically or digestion derived toxicant.

In some embodiments, the toxic agent is a stimulant. In some embodiments, the sequestration agent binds to the stimulant with a $K_a$ of at least about $1\times10^3M^{-1}$, $1\times10^4M^{-1}$, $1\times10^5M^{-1}$, $1\times10^6M^{-1}$, $1\times10^7M^{-1}$, $1\times10^8$ $M^{-1}$, or $1\times10^9$ $M^{-1}$. In some embodiments, the stimulant is selected from the group consisting of amphetamines, methamphetamine, Ritalin, phencyclidine, cocaine, caffeine, 3,4-methylenedioxy-methamphetamine (MDMA), and any pharmaceutically acceptable salts, and any combinations thereof.

In some embodiments, the CNS active agent binds to the toxic agent with a $K_a$ of at least about $1\times10^3M^{-1}$, $1\times10^4M^{-1}$, $1\times10^5M^{-1}$, $1\times10^6M^{-1}$, $1\times10^7M^{-1}$, $1\times10^8$ $M^{-1}$, or $1\times10^9$ $M^{-1}$.

In some embodiments, the sequestration agent binds to the CNS active agent with a $K_a$ of at least about $1\times10^3M^{-1}$, $1\times10^4M^{-1}$, $1\times10^5M^{-1}$, $1\times10^6M^{-1}$, $1\times10^7M^{-1}$, $1\times10^8$ $M^{-1}$, or $1\times10^9$ $M^{-1}$.

In some embodiments, the sequestration agent (e.g., Compound A or a pharmaceutically acceptable salt thereof) is administered at about 1 mg/kg to about 2,000 mg/kg. In some embodiments, the sequestration agent (e.g., Compound A or a pharmaceutically acceptable salt thereof) is administered at about 1 mg/kg to about 1,000 mg/kg. In some embodiments, the sequestration agent (e.g., Compound A or a pharmaceutically acceptable salt thereof) is administered at about 1 mg/kg to 500 about mg/kg. In some embodiments, the sequestration agent (e.g., Compound A or a pharmaceutically acceptable salt thereof) thereof is administered at about 10 mg/kg to about 300 mg/kg.

In some embodiments, the CNS active agent (e.g., naloxone) is administered at about 0.1 μg/kg to about 1,000 μg/kg. In some embodiments, the CNS active agent is administered at about 1 μg/kg to about 500 μg/kg. In some embodiments, the CNS active agent is administered at about 100 μg/kg to about 500 μg/kg. In some embodiments, the CNS active agent is administered at about 100 μg/kg to about 400 μg/kg.

In some embodiments, the sequestration agent is Compound A or a pharmaceutically acceptable salt thereof, wherein Compound A or a pharmaceutically acceptable salt thereof is administered at about 1 mg/kg to about 2,000 mg/kg.

In some embodiments, the CNS active agent is naloxone or a pharmaceutically acceptable salt thereof, wherein the naloxone or a pharmaceutically acceptable salt thereof is administered at about 0.1-1,000 μg/kg.

In some embodiments, the sequestration agent (e.g., Compound A or a pharmaceutically acceptable salt thereof) is present at about 10 mg/kg to 500 mg/kg. In some embodiments, the CNS active agent (e.g., naloxone or a pharmaceutically acceptable salt thereof) is present at about 100-600 μg/kg. In some embodiments, the sequestration agent or a pharmaceutically acceptable salt thereof is administered at about 10 mg/kg to 300 mg/kg. In some embodiments, the CNS active agent or a pharmaceutically acceptable salt thereof is administered at about 100-400 μg/kg.

In some embodiments, the CNS active agent is provided in a pharmaceutical composition, further including at least one pharmaceutically acceptable excipient. In some embodiments, the sequestration agent is provided in a pharmaceutical composition, further including at least one pharmaceutically acceptable excipient. In some embodiments, the CNS active agent and sequestration agent are co-formulated in a pharmaceutical composition, further including at least one pharmaceutically acceptable excipient. In some embodiments, the pharmaceutical composition comprises Compound A or a pharmaceutically acceptable salt thereof, wherein Compound A or a pharmaceutically acceptable salt thereof is present at about 0.01% by weight to about 20% by weight. In some embodiments, the pharmaceutical composition comprises naloxone or a pharmaceutically acceptable salt thereof, wherein the naloxone or a pharmaceutically acceptable salt thereof is present at about 0.01% by weight to about 20% by weight.

In some embodiments, the pharmaceutical composition is in a form suitable for oral, intravenous, intramuscular, subcutaneous, intramedullary, intrathecal, intraperitoneal, intranasal, ophthalmic, pulmonary, transmucosal, transdermal, or topical administration. In some embodiments, the pharmaceutical composition is a liquid dosage form. In some embodiments, the pharmaceutical composition is a solid dosage form.

In some embodiments, the methods described herein comprise administration of the pharmaceutical composition in a number of administration methods, for example orally, intravenously, intramuscularly, subcutaneously, intramedullary, intrathecally, intraperitoneally, intranasal, ophthalmic, pulmonary, transmucosal, transdermal, topically, sublingually or buccally. In some embodiments, the subject is a human.

In some embodiments, the method further comprises monitoring the subject to determine whether subsequent administration of a CNS active agent is needed. In some embodiments, the monitoring comprises measuring the subject for abnormal heartrate, respiratory rate, appetite, cognitive capacity, or any combination thereof. In some embodiments, the method further comprises administration of a CNS active agent (e.g., naloxone) after the monitoring. In some embodiments, the method provides alleviation of narcotic intoxication. In some embodiments, the method provides alleviation of an opioid overdose, stimulant overdose, or a symptom thereof. In some embodiments, alleviation of an opioid overdose, stimulant overdose, comprises restoration of normal respiration rate. In some embodiments, normal respiration rate comprises at least about 15 to 20 breaths per minute. In some embodiments, normal respiration rate comprises at least about 12 to 16 breaths per minute. In some, embodiments, the alleviation of narcotic intoxication comprises restoration of appetite. In some embodiments, alleviation of narcotic intoxication prevents re-narcotization. In some embodiments, the method further comprises at least a second administration of a CNS active agent.

In some embodiments, the sequestration agent or a pharmaceutically acceptable salt thereof is administered at about 1 mg/kg to 2,000 mg/kg. In some embodiments, the sequestration agent or a pharmaceutically acceptable salt thereof is administered at about 10 mg/kg to 500 mg/kg. In some embodiments, the CNS active agent or a pharmaceutically acceptable salt thereof is administered at about 1-1,000 μg/kg. In some embodiments, the CNS active agent or a pharmaceutically acceptable salt thereof is administered at about 100-600 μg/kg. In some embodiments, the sequestration agent comprises Compound A, or any derivative thereof. In some embodiments, the CNS active agent comprises naloxone or a pharmaceutically acceptable salt thereof. In some embodiments, the method further comprises administration of the CNS active agent. In some embodiments, the administration of the CNS active agent comprises at least about 1, 2, 3, or 4 doses over 8 hours. In some embodiments, the administration of the CNS active agent comprises at least about 0.4 mg, 2 mg, 4 mg, 8 mg, 12 mg, or 16 mg over 8 hours.

Provided herein the disclosure provides a kit comprising a composition, the composition comprising i) a therapeutically effective amount of an CNS active agent; ii) a therapeutically effective amount of a sequestration agent wherein the therapeutically effective amount is an amount effective to sequester at least one toxic agent, and wherein the kit provides instructions to administer the composition to a subject in need thereof. In some embodiments, the sequestration agent and the CNS active agent are in the same formulation. In some embodiments, the sequestration agent and the CNS active agent are in different formulations. In some embodiments, the sequestration agent or a pharmaceutically acceptable salt thereof is administered at about 1 mg/kg to 2,000 mg/kg to the subject in need thereof. In some embodiments, the sequestration agent or a pharmaceutically acceptable salt thereof is administered at about 10 mg/kg to 500 mg/kg to the subject in need thereof. In some embodiments, the sequestration agent is Compound A or any derivative thereof. In some embodiments, the CNS active agent or a pharmaceutically acceptable salt thereof is administered at about 0.11-1,000 μg/kg to a subject in need thereof. In some embodiments, the sequestration agent is Compound A or any derivative thereof. In some embodiments, the CNS active agent or a pharmaceutically acceptable salt thereof is administered at about 100-600 μg/kg to a subject in need thereof. In some embodiments, the CNS active agent is naloxone. In some embodiments, the subject is human.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Definitions

Figure 1:
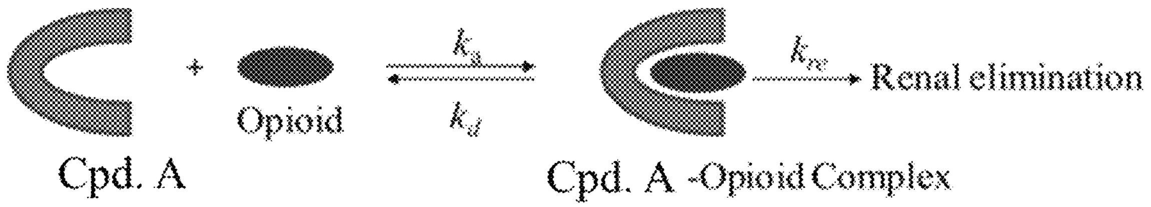
FIG. 1 provides a schematic of Compound A binding to a compound of interest. For example, Compound A binds a synthetic opioid (e.g., fentanyl) with a binding constant $K_a$ of 1×107 M−1, forming a complex and effectively sequestering the synthetic opioid, and subsequently removed from the blood by the kidneys.

By "antagonist" it is intended to mean a receptor ligand that does not provoke a biological response upon binding to a receptor, but which blocks or dampens (decreases, lessens, etc.) agonist-mediated responses. (An "agonist" is a ligand that binds to a receptor and triggers a response, i.e., an agonist produces an action, often mimicking the action of a naturally occurring substance.) Antagonists thus have affinity but little or no efficacy for their cognate receptors, and binding of an antagonist to a receptor will disrupt the interaction and inhibit the function of an agonist or inverse agonist at receptors. Antagonist activity may be reversible or irreversible depending on the longevity of the antagonist-receptor complex, which, in turn, depends on the nature of antagonist receptor binding.

As used herein, the term "about" or "approximately" can mean within an acceptable error range for the particular value as determined by one of ordinary skill in the art, which will depend in part on how the value is measured or determined, e.g., the limitations of the measurement system. For example, "about" can mean plus or minus 10%, per the practice in the art. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

As used herein, the term "drug of abuse" is intended to mean any substance the excessive consumption or administration of which can result in a diagnosis of substance dependence or substance abuse (e.g., substance use disorder), or intoxication as defined herein or as defined by the current DSM Criteria promulgated by the American Psychiatric Association or equivalent criteria. Drugs of abuse include, without limitation, cocaine, amphetamines, methamphetamine, methylphenidate, heroin, codeine, hydrocodone, nicotine, alcohol, prescription medication (e.g., Percodan®, Percocet®), marijuana, tobacco, methadone. For clarity, it is understood that drugs of abuse include, without limitation, heroin, cocaine, methamphetamines, opioids, fentanyl, fentanyl analogues, fentanyl derivatives, fentanyl metabolites, carfentanil, or any combination thereof. Furthermore, drugs of abuse can include, but not necessarily limited to those drugs listed by the National Institute of Health (NIH) and the National Institute of Drug Abuse (NIDA). Exemplary drugs of abuse noted by NIDA can include, but are not limited to, alcohol, ayahuasca, CNS depressants, cocaine, N, N-Dimethyltryptamine (DMT), Gamma-hydroxybutyrate (GHB), hallucinogens, heroin, inhalants, ketamine, khat, kratom, Lysergic acid diethylamide (LSD), marijuana (cannabis), MDMA (molly/ecstasy), mescaline (peyote), methamphetamine, dextromethorphan, loperamide, PCP, psilocybin, Rohypnol, salvia, steroids, synthetic cannabinoids, synthetic cathinones (bath salts), nicotine, tobacco, extroamphetamine, methylphenidate, or dexmethylphenidate.

The term "subject" or "patient" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse. In one embodiment, a non-human animal is a mouse.

The terms "treat", "treating" or "treatment", as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents, excipients, preservatives or lubricants used in formulating pharmaceutical products.

The term "pharmaceutically acceptable salts" denotes salts which are not biologically or otherwise undesirable. Pharmaceutically acceptable salts include both acid and base addition salts. A "pharmaceutically acceptable salt" can refer to a formulation of a compound that does not cause significant irritation to an organism to which it is administered and/or does not abrogate the biological activity and properties of the compound.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Combinations Comprising a Central Nervous System (CNS) Active Agent and Sequestration Agent The present disclosure is related to a method of use, composition, and kits comprising a combination of a sequestration agent (e.g., a cyclic cucurbituril, an acyclic cucurbituril, a pillararene, a cyclodextrin, a calixarene, or the like) and a CNS active agent.

Single agent use of CNS active agents or sequestration agents to antedate the effects of toxic agents, may not be sufficient. For example, Naloxone has a short half-life (~60 min) and is becoming less effective against newer synthetic opioids that have a longer half-life, such as fentanyl with a half-life of 10-12 hrs. This often results in a secondary overdose phenomenon known as renarcotization. To avoid renarcotization, the standard of care is to administer higher and more frequent doses of naloxone. However, this can lead to a secondary complication called precipitated opioid withdrawal (POW), a serious and sometimes life-threatening condition. Moreover, the relative binding affinities of some CNS active agents to their receptor may not be sufficient to completely displace the toxic agent.

The present disclosure utilizes a combination of sequestering agents and CNS active agents to displace and clear toxic agents. Without wishing to be bound by any theory of mechanism of action, it is contemplated that the CNS active agent displaces the toxic agent from its receptor (e.g., opiate receptor), and the sequestration agent captures and clears the toxic agent, e.g., from a body of a subject. In some embodiments, the sequestration agent and CNS active agent are co-formulated and/or co-administered, or are administered in close proximity to each other (e.g., less than 5 minutes apart). In some embodiments, the CNS active agent is administered first so as to free the toxic agent from its receptor, followed by administration of the sequestration agent (preferably less than about 5 minutes thereafter) which captures and eliminates such toxic agents from a subject's circulation. In some embodiments, administration of a sequestration agent in temporal proximity to the CNS active agent prevents renarcotinzation and facilitates clearance of the toxic agent from the subject undergoing treatment.

In some embodiments, the present disclosure provides therapeutically effective treatment of carfentanil intoxication without requiring the administration substantially higher amounts of naloxone (than required to treat fentanyl intoxication) and without requiring repeated administration of naloxone to prevent re-narcotization. Thus, the results demonstrate that (1) a sequestrant described herein (e.g., Compound A) was able to rapidly sequester and clear a toxic agent (e.g., an opioid such as Carfentanil); and that (2) a CNS active agent (e.g., naloxone) was effective at binding to the opioid receptor and displacing the toxic agent, without the need for multiple administrations.

The present disclosure is related to the use of compositions that are further described below for reversal of the effects of intoxicating agents, as well as for reversal of the effects of other agents that are more fully described herein. In some embodiments, the disclosure provides embodiments that are suitable for use in reversal of drug-induced neuromuscular block, or for reversal of anesthesia, or for reversal of the effects of an intoxication by a drug of abuse, or an antidepressant or other agent. In some embodiments, the disclosure includes reversing the effect of one or more agents which include but are not limited to opioids, cocaine, heroin, amphetamines, methamphetamine, phencyclidine [PCP]), drugs used in perioperative medicine, including but not necessarily limited to local anesthetics, beta-blockers, neurolepts, or a combination of any of said agents. In non-limiting and illustrative embodiments, the reversal is achieved by administering to the individual a composition comprising a sequestering agent which is further described below. In one embodiment the method encompasses reversal of intoxication by cocaine, fentanyl, fentanyl analogues, fentanyl derivatives, or methamphetamine, or any combination thereof. Thus, in embodiments, a composition comprising one or a combination of compounds described herein is administered to an individual in need of treatment due to intoxication of drugs of abuse.

By the combination of a sequestering agent and a CNS active agent, it is ensured that preparations according to the present disclosure provide an efficient reduction of drug intoxication associated symptoms and that at the same time, a need for repeated administration of a CNS active agent (e.g., naloxone) is at least significantly reduced.

Provided herein, the disclosure provides a pharmaceutical composition for treating intoxication, overdose, or a symptom thereof due to use of at least one drug of abuse in a human comprising i) a sequestration agent or a pharmaceutically acceptable salt thereof; ii) a central nervous system (CNS) active agent or a pharmaceutically acceptable salt thereof; and iii) a pharmaceutically acceptable excipient, wherein the sequestration agent is selected from a cyclic or acyclic cucurbituril pillararene, cyclodextrin, or calixarene. In some embodiments, the sequestration agent is selected from a cyclic or acyclic cucurbituril or pillararene.

Provided herein, the disclosure provides a pharmaceutical composition for treating intoxication due to use of at least one drug of abuse or a symptom thereof comprising i) a sequestration agent or a pharmaceutically acceptable salt thereof in an amount sufficient to sequester the at least one toxic agent; and ii) a CNS active agent or a pharmaceutically acceptable salt thereof, wherein the sequestration agent is preferably selected from a cucurbituril, pillararene, cyclodextrin, or calixarene. In some embodiments, the sequestration agent is selected from a cyclic or acyclic cucurbituril or pillararene.

Provided herein, the disclosure provides a pharmaceutical composition for treating intoxication due to use of at least one drug of abuse or a symptom thereof comprising i) a sequestration agent or a pharmaceutically acceptable salt thereof in an amount sufficient to sequester the at least one toxic agent; and ii) a CNS active agent or a pharmaceutically acceptable salt thereof.

Provided herein, the disclosure provides a method of treating a suspected opioid overdose or symptom thereof in a human, the method comprising administering a therapeutically effective amount of a sequestration agent or a pharmaceutically acceptable salt thereof co-administered with a therapeutically effective amount of an CNS active agent or a pharmaceutically acceptable salt thereof, wherein the administration is effective to treat the suspected opioid overdose in the human in need thereof. In some embodiments, the opioid is selected from a group consisting of fentanyl, fentanyl analogs, carfentanil, heroin, morphine sufentanyl, acetylfentanyl, alfentanil, and any combinations thereof.

Provided herein, the disclosure provides a method of treating an intoxication of a drug of abuse or symptom thereof in a human, the method comprising co-administering a therapeutically effective amount of a sequestration agent or a pharmaceutically acceptable salt thereof with a therapeutically effective amount of an CNS active agent or a pharmaceutically acceptable salt thereof, wherein the administration is effective to treat the stimulant overdose or symptom thereof in the human in need thereof. In some embodiments, the stimulant is selected from a group consisting of amphetamines, methamphetamine, Ritalin, cocaine, caffeine, phencyclidine, MDMA, and any combinations thereof.

Provided herein, the disclosure provides a method of treating a suspected overdose or symptom thereof in a subject, comprising co-administering a therapeutically effective amount of a sequestration agent or a pharmaceutically acceptable salt thereof with a therapeutically effective amount of an CNS active agent or a pharmaceutically acceptable salt thereof, wherein the subject has a suspected overdose from a plurality of drugs of abuse. In some embodiments, the plurality of drugs comprises at least 1, at least 2, at least 3, at least 4 drugs of abuse.

Provided herein, the disclosure provides a method of treating a suspected opioid overdose in a subject, the method comprising co-administering a sequestration agent or a pharmaceutically acceptable salt thereof with an CNS active agent or a pharmaceutically acceptable salt thereof, wherein the CNS active agent is administered less than 5 minutes after the sequestration agent.

Sequestering Agents

Provided herein, are sequestering agents of the present disclosure. Sequestering agents (also referred to herein interchangeably as sequestration agents) are molecules used in the treatment of diseases caused by excess levels of toxic substances. Sequestering agents are used in the treatment of drug abuse, intoxication by a drug of abuse, use of a drug of abuse, drug overdose, ingestion, or otherwise taking in or exposure to a drug of abuse. In addition, sequestering agents can be used to bind to molecules of interest in order to provide a means to remove the molecule of interest from the body often through renal clearance. Sequestering agents can bind to a molecule of interest with a binding constant represented by $K_a$ ($M^{-1}$), wherein $K_a=k_{on}/k_{off}$.

Sequestration agents may be used remove toxicants and treat drug intoxication, as an alternative to utilizing bioreceptor-drug antagonism or pharmacokinetic (PK) approaches. The article "Supramolecular hosts as in vivo sequestration agents for pharmaceuticals and toxins" (Chem. Soc. Rev. 2020, 49, 7516) the entire disclosure of which, except for any definitions, disclaimers, disavowals, and inconsistencies, is incorporated herein by reference, provides exemplary sequestration agents. See also, Thevathasan, T.; Grabitz, S. D.; Santer, P.; Rostin, P.; Akeju, O.; Boghosian, J. D.; Gill, M.; Isaacs, L.; Cotton, J. F.; Eikermann, M. "Calabadion 1 selectively reverses respiratory and central nervous system effects of fentanyl in a rat model," *British Journal of Anaesthesia* 2020, S0007-0912(20) 30134-3.

In some embodiments, the sequestration agent can be a cyclodextrin, an acyclic cucurbituril, a cyclic cucurbituril, a pillararene, a calixarene, or cyclodextrin. In some embodiments, the sequestration agent is a cucurbituril. In some embodiments, the sequestration agent is an acyclic cucurbituril. In some embodiments, the sequestration agent is a cyclic cucurbituril. In some embodiments, the sequestration agent is apillararene. In some embodiments, the sequestration agent is a calixarene. In some embodiments, the sequestration agent is a cyclodextrin.

In some embodiments, the sequestering agent can comprise the following structure:

Compound A

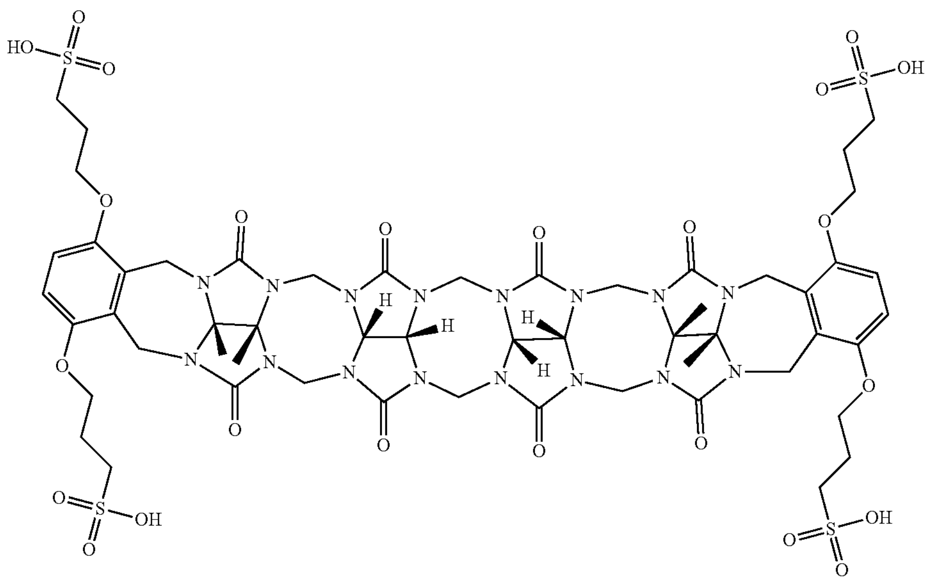

Cucurbiturils molecular containers are macrocycles comprising n glycoluril monomers linked by 2n methylene groups that can be prepared by the condensation of glycoluril and formaldehyde under strongly acidic conditions. The molecular structure of cucurbiturils features a central hydrophobic cavity that is guarded by two symmetry equivalent ureidyl carbonyl portals of highly negative electrostatic potential. Thus, cucurbiturils show a preference to bind molecules that feature a central hydrophobic domain that is flanked by cationic (e.g., ammonium) groups. Binding of molecules are mediated by the hydrophobic effects and ion-dipole interactions. In some cases, ultra tight binding ($K_a$>$10^{12}$ $M^{-1}$) has been observed in some cucurbiturils designed to bind to adamantane, diamantine, and ferrocene.

Acyclic cucurbiturils molecular containers are similar but exhibit higher water solubility and can provide a more flexible binding cavity that can accommodate larger molecules. Acyclic cucurbiturils mediate tight binding through interaction of hydrophobic cations but can also be modified synthetically. These molecules feature a central glycoluril tetramer to impart a C-shape and hydrophobic cation binding properties, presented by two terminal aromatic side walls to engage in cation -π, CH-π, and π-π interaction with molecules. Four sodium sulfonate arms help enhance water solubility and promote secondary electrostatic interactions between the cucurbituril and the bound molecule.

Pillararenes are macrocyclic molecules composed of n aromatic rings connected by n methylene bridges at the para positions. Small pillararenes bind to narrow n-alkane molecules, whereas larger pillararenes can bind to aromatics, viologens, and alicyclic molecules. Exemplary pillararenes are provided herein (Xue et. Al, Angewandte Chemie, 2020), which has been incorporated by reference in its entirety.

In some embodiments, the sequestration agent is a pillararene of the following structure:

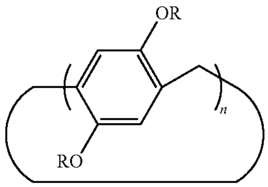

wherein n is an integer from 5-8, and R═$SO_3H$ or a salt there (e.g., $SO_3Na$), or —$CH_2COOH$ or a salt thereof (e.g., $CH_2COONa$).

In some embodiments, n=5. In some embodiments, n=6. In some embodiments, n=7. In some embodiments, n=8. In some embodiments, n=6 and R═$SO_3H$ or $SO_3Na$, and the compound is referred to herein as Compound B.

In some embodiments, the sequestration agent is a cyclic cucurbituril of the following formula:

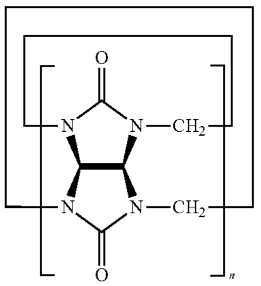

wherein n is an integer from 5-8.

In some embodiments, n=5. In some embodiments, n=6. In some embodiments, n=7. In some embodiments, n=8. In some embodiments, n=7, and the compound is referred to herein as Compound C.

In some embodiments, the sequestration agent binds to a toxic agent (e.g., a drug of abuse) with a $K_a$ of at least about $1\times10^3$ $M^{-1}$, $1\times10^4$ $M^{-1}$, $1\times10^5$ $M^{-1}$, $1\times10^6$ $M^{-1}$, $1\times10^7$ $M^{-1}$, $1\times10^8$ $M^{-1}$ or $1\times10^9$ $M^{-1}$. In some embodiments, the sequestration agent binds to a toxic agent (e.g., a drug of abuse) with a $K_a$ of about $1\times10^3$ $M^{-1}$-$1\times10^4$ $M^{-1}$, $1\times10^3$ $M^{-1}$-$1\times10^5$ $M^{-1}$, $1\times10^3$ $M^{-1}$-$1\times10^6M^{-1}$, $1\times10^3$ $M^{-1}$-$1\times10^7$ $M^{-1}$, $1\times10^3$ $M^{-1}$-$1\times10^8M''^1$, $1\times10^4$ $M^{-1}$-$1\times10^5$ $M^{-1}$, $1\times10^4$ $M^{-1}$-$1\times10^6$ $M^{-1}$, $1\times10^4$ $M^{-1}$-$1\times10^7$ $M^{-1}$, $1\times10^4$ $M^{-1}$-$1\times10^8$ $M^{-1}$, $1\times10^5$ $M^{-1}$-$1\times10^6$ $M^{-1}$, $1\times10^5$ $M^{-1}$-$1\times10^7$ $M^{-1}$, $1\times10^5$ $M^{-1}$-$1\times10^8$ $M^{-1}$, $1\times10^6$ $M^{-1}$-$1\times10^7$ $M^{-1}$, $1\times10^6$ $M^{-1}$-$1\times10^8M^{-1}$ or $1\times10^7$-$1\times10^8$ $M^{-1}$ or $1\times10^7$ $M^{-1}$-$1\times10^9M^{-1}$.

Central Nervous System (CNS) Active Agents

CNS active agents can include compounds, molecules or drugs, that affect the central nervous system. Exemplary CNS active agents may include, but are not limited to anesthetics, anticonvulsants, antiemetics, CNS stimulants, muscle relaxants, narcotic analgesics (pain relievers), non-narcotic analgesics (such as acetaminophen and NSAIDs), opioid receptor antagonists, and sedatives. In some embodiments, the CNS active agent can be an opioid receptor antagonist.

Opioid receptor antagonist are molecules are used in the reversal of life-threatening opioid toxicity in which an individual has opioid toxicity. Exemplary opioid receptor antagonists can be, but are not limited to, naloxone (Narcan® or Evzio®), naltrexone, and Suboxone®.

Provided herein in some embodiments, the composition comprises an opioid receptor antagonist.

The disclosed compositions may comprise an opioid receptor antagonist, such as naloxone, naltrexone, nalmefene, nalorphine, nalbuphine, naloxoneazinen, methylnaltrexone, ketylcyclazocine, norbinaltorphimine, naltrindol, 6-13-naloxol, 6-13-naltrexol, or pharmaceutically acceptable salts thereof. In some embodiments, the opioid receptor antagonist is a mu opioid receptor antagonist, such as naloxone or naltrexone, or pharmaceutically acceptable salts thereof. In one embodiment, the opioid receptor antagonist is naloxone, naloxone base, or a pharmaceutically acceptable salt thereof, including naloxone HCl, naloxone HCl dihydrate, or combinations thereof. Naloxone hydrochloride is a synthetic congener of oxymorphone. In structure it differs from oxymorphone in that the methyl group on the nitrogen atom is replaced by an allyl group. It is known chemically as 17-allyl-4,5 α-epoxy, 3-14-dihydroxymorphinan-6-one hydrochloride. It has a molecular weight of 363.84, contains four chiral centers, and the following structural formula: $C_{19}H_{22}ClNO_4$.

Naloxone hydrochloride occurs as a white to slightly off-white powder, and is soluble in water, in dilute acids, and in strong alkali; slightly soluble in alcohol; practically insoluble in ether and in chloroform. Naloxone prevents or reverses the effects of opioids including respiratory depression, sedation and hypotension. Also, it can reverse the psychotomimetic and dysphoric effects of agonist-antagonists such as pentazocine. Naloxone is an essentially pure opioid receptor antagonist, i.e., it does not possess the "agonistic" or morphine-like properties characteristic of other opioid receptor antagonists. When administered in usual doses in the absence of opioids or agonistic effects of other opioid receptor antagonists, it exhibits essentially no pharmacologic activity. Naloxone has not been shown to produce tolerance or cause physical or psychological dependence. In the presence of physical dependence on opioids, naloxone will produce withdrawal symptoms. However, in the presence of opioid dependence, withdrawal symptoms will appear within minutes of naloxone administration and will subside in about 2 hours. The severity and duration of the withdrawal syndrome are related to the dose and route of administration of naloxone and to the degree and type of dependence. While the mechanism of action of naloxone is not fully understood, in vitro evidence suggests that naloxone antagonizes opioid effects by competing for the mu, kappa, and sigma opiate receptor sites in the CNS, with the greatest affinity for the mu receptor. Other opioid receptor antagonists, for example, cyclazocine and naltrexone, both of which have cyclopropylmethyl substitutions on the nitrogen, retain much of their efficacy and their durations of action are much longer, approaching 24 hours after demonstration.

Naloxone has a short half-life (~60 min) and is becoming less effective against newer synthetic opioids that have a longer half-life, such as fentanyl with a half-life of 10-12 hrs. This often results in a secondary overdose phenomenon known as renarcotization.

To avoid renarcotization, the standard of care is to administer higher and more frequent doses of naloxone. However, this can lead to a secondary complication called precipitated opioid withdrawal (POW), a serious and sometimes life-threatening condition. Therefore, it is necessary to find other treatments that would be able to remove the drug of abuse to effectively treat fentanyl intoxication or overdose.

Treatment of methamphetamine intoxication or overdose with naloxone is not sufficiently effective. Thus, treatment of polydrug intoxication or overdose with naloxone may not be sufficient. Therefore, it is necessary to find other treatments that would be able to remove the drug of abuse to effectively treat polydrug intoxication or overdose.

Naltrexone is another opioid receptor antagonist. However, equiantagonistic doses of other opioid receptor antagonists, including but not limited to naloxone, nalmephene, cyclazocine, and levallorphan can be utilized in accordance with the present disclosure. The ratio of such other antagonists to a particular opioid agonist can be readily determined without undue experimentation by one skilled in the art who desires to utilize a different opioid receptor antagonist than naltrexone, and the ratio of opioid antagonist to opioid agonists is exemplified and discussed in detail herein. Those skilled in the art may determine such ratios of other antagonists to opioid agonists, e.g., by conducting the same or similar clinical studies set forth in the examples appended herein. Thus, combinations of opioid receptor antagonists/opioid agonists which are orally, intravenously, sublingually, intramuscularly, or subcutaneously administered in ratios which are equivalent to the ratio of, e.g., naltrexone to hydrocodone set forth herein are considered to be within the scope of the present disclosure and within the scope of the appended claims. For example, in certain embodiments of the disclosure naloxone is utilized as the opioid receptor antagonist, the amount of naloxone included in the dosage form being large enough to provide an equiantagonistic effect as naltrexone were included in the combination.

In some embodiments, naloxone (e.g., Narcan®) is administered orally, as an injectable, or as an inhalant. In some embodiments, the opioid receptor antagonist can be Suboxone®, naltrexone, or methylnaltrexone.

In some embodiments, the CNS active agent is a benzodiazepine. In some embodiments, the CNS active agent is a benzodiazepine selected from the group consisting of: lorazepam, klonopin, clonazepam, diazepam, alprazolam, chlordiazepoxide, clorazepate, halazepam, oxazepam, prazepam, and quazepam, or a pharmaceutically acceptable salt thereof.

In some embodiments, the CNS active agent is an antihistamine. In some embodiments, the CNS active agent is an antihistamine selected form the group consisting of: cetirizine, diphenhydramine, fexofenadine, loratadine, desloratadine, clemastine, chlorpheniramine, levocetirizine, cyproheptadine, carbinoxamine, emedastine, levocabastine, or pharmaceutically acceptable salts thereof.

In some embodiments, the CNS active agent is ketamine or a pharmaceutically acceptable salt thereof.

In some embodiments, the CNS active agent is atropine or a pharmaceutically acceptable salt thereof. In some embodiments, the CNS active agent is scopolamine or a pharmaceutically acceptable salt thereof.

Method of Treatment

Provided in this disclosure is a method to treat a subject with intoxication by a drugs of abuse. In one embodiment, the disclosure provides a method of treating intoxication by a drug of abuse in a subject, the method comprising administering a therapeutically effective amount of a sequestering agent or a pharmaceutically acceptable salt thereof, in combination with a therapeutically effective amount of a CNS active agent or a pharmaceutically acceptable salt thereof, wherein the administration is effect to treat the intoxication or overdose by a toxic agent, e.g., a drug of abuse in a subject in need thereof. In some embodiments, the CNS active agent and sequestering agent are administered within 0 minutes, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, or 60 minutes. In some embodiments, the sequestering agent is administered first. In some embodiments the CNS active agent is administered first. In some embodiments, the sequestering agent and CNS active agent are administered together. In some embodiments, the CNS active agent is administered first, followed by the sequestering agent which is preferably administered less than 5 minutes after the CNS active agent (e.g., simultaneously, 30 seconds, 1 minute, 1.5 minutes, 2 minutes, 2.5 minutes, 3 minutes, 3.5 minutes, 4 minutes or 4.5 minutes).

Provided herein is a method of treating intoxication by a toxic agent, e.g., a drug of abuse, wherein the method comprises administering i) an CNS active agent; and ii) a sequestering agent. In some embodiments, the CNS active agent and sequestering agent are administered within 0 minutes, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, or 60 minutes. In some embodiments, the sequestering agent is administered first. In some embodiments the CNS active agent is administered first. In some embodiments, the sequestering agent and CNS active agent are administered together.

Provided herein, is a method of treating intoxication by a toxic agent, e.g., a drug of abuse comprising administering a therapeutically effective amount of a CNS active agent to treat the acute effects of intoxication by a drug of abuse and a therapeutically effective amount of the sequestering agent to bind and remove the drug from the blood. In some embodiments, the CNS active agent and sequestering agent are administered within 0 minutes, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, or 60 minutes. In some embodiments, the sequestering agent is administered first. In some embodiments the CNS active agent is administered first. In some embodiments, the sequestering agent and CNS active agent are administered together.

Provided herein in some embodiments is a method of treating intoxication by a drug of abuse, wherein the method comprises administering a composition comprising a CNS active agent and a sequestering agent to a subject in need thereof, wherein the composition prevents narcotization. In some embodiments, the composition prevents renarcotization more effectively than administration of a CNS active agent alone.

In some embodiments, additional administrations of a CNS active agent can be provided to alleviate the symptoms of a drug overdose. In the case of opioids, depressed heart rate and depressed respiration rate can be indicative of an opioid overdose. In these cases, a clinician would recognize these symptoms and prescribe an additional dose of naloxone until the symptoms have stabilized. In the case of stimulant drugs, such as methamphetamine, associated symptoms include but are not limited to, elevated heart rate, elevated respiration, and excited delirium.

In some embodiments, additional administrations of a sequestration agent can be provided to alleviate the symptoms of a drug overdose, drug intoxication, or a symptom thereof. In the case of opioids, depressed heart rate and depressed respiration rate can be indicative of an opioid overdose. In these cases, a clinician would recognize these symptoms and prescribe an additional dose of naloxone until the symptoms have stabilized. In the case of stimulant drugs, such as methamphetamine, associated symptoms include but are not limited to, elevated heart rate, elevated respiration, and excited delirium.

In some embodiments, after administration of the sequestering agent and the CNS active agent, a clinician monitors the subject to determine if an additional dose of naloxone or a CNS active agent is needed to relive the symptoms related to an overdose.

In some embodiments, the methods and pharmaceutical compositions of the disclosure may be administered to a subject by any suitable route, for example parentally by intravenous (i.v.) infusion, bolus injection, intramuscularly, subcutaneously, intraperitoneally, orally, inhalation, sublingually, or buccally.

U.S. application Ser. No. 15/417,785 (US 2017/0137431), the entire disclosure of which, except for any definitions, disclaimers, disavowals, and inconsistencies, is incorporated herein by reference, provides exemplary cucurbiturils and sequestering agents. In some embodiments, the sequestering agent can be a cucurbituril, a pillararene, a cyclodextrin, or a calixarene. In some embodiments, the sequestering agent can be a cyclic or acyclic cucurbituril. In some embodiments, the sequestering agent comprises the structure:

Compound A

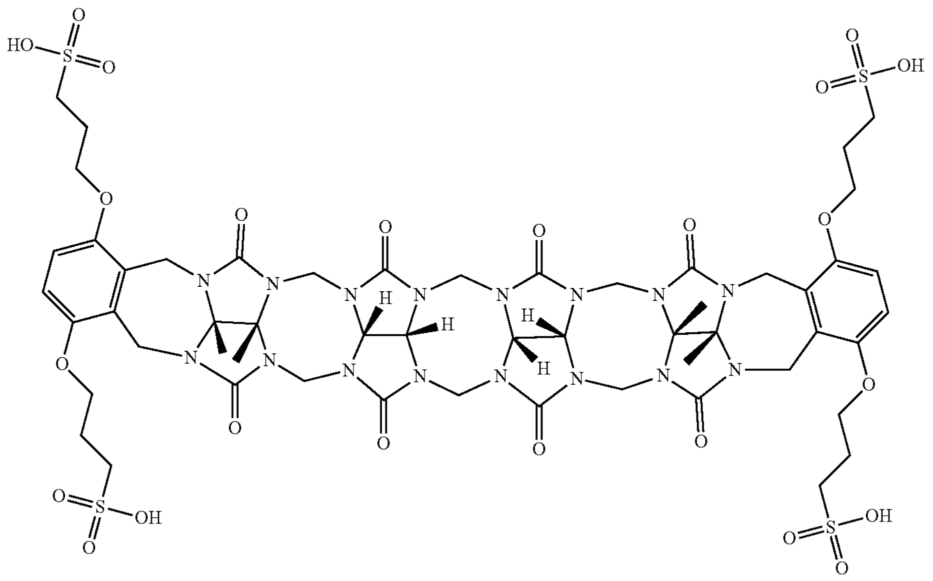

In some embodiments, the sequestering agent or a pharmaceutically acceptable salt thereof is adminstered at about 0.05 mg/kg to 500 mg/kg. In some embodiments, sequestering agent is adminstered at about 0.05 mg/kg-50 mg/kg, 50-60 mg/kg, 50-70 mg/kg, 50-80 mg/kg, 50-90 mg/kg, 50-100 mg/kg, 50-120 mg/kg, 50-140 mg/kg, 50-160 mg/kg, 50-180 mg/kg, 50-200 mg/kg, 50-220 mg/kg, 50-240 mg/kg, 50-260 mg/kg, 50-280 mg/kg, 50-300 mg/kg, 50-350 mg/kg, 50-400 mg/kg, 50-450 mg/kg, 50-500 mg/kg, 60-70 mg/kg, 60-80 mg/kg, 60-90 mg/kg, 60-100 mg/kg, 60-120 mg/kg, 60-140 mg/kg, 60-160 mg/kg, 60-180 mg/kg, 60-200 mg/kg, 60-220 mg/kg, 60-240 mg/kg, 60-260 mg/kg, 60-280 mg/kg, 60-300 mg/kg, 60-350 mg/kg, 60-400 mg/kg, 60-450 mg/kg, 60-500 mg/kg, 80-90 mg/kg, 80-100 mg/kg, 80-120 mg/kg, 80-140 mg/kg, 80-160 mg/kg, 80-180 mg/kg, 80-200 mg/kg, 80-220 mg/kg, 80-240 mg/kg, 80-260 mg/kg, 80-280 mg/kg, 80-300 mg/kg, 80-350 mg/kg, 80-400 mg/kg, 80-450 mg/kg, 80-500 mg/kg, 100-120 mg/kg, 100-130 mg/kg, 100-140 mg/kg, 100-150 mg/kg, 100-160 mg/kg, 100-180 mg/kg, 100-200 mg/kg, 100-220 mg/kg, 100-240 mg/kg, 100-260 mg/kg, 100-280 mg/kg, 100-300 mg/kg, 100-350 mg/kg, 100-400 mg/kg, 100-450 mg/kg, 100-500 mg/kg, 140-160 mg/kg, 140-180 mg/kg, 140-200 mg/kg, 140-220 mg/kg, 140-240 mg/kg, 140-260 mg/kg, 140-280 mg/kg, 140-300 mg/kg, 140-350 mg/kg, 140-400 mg/kg, 140-450 mg/kg, 140-500 mg/kg, 160-200 mg/kg, 160-220 mg/kg, 160-240 mg/kg, 160-260 mg/kg, 160-280 mg/kg, 160-300 mg/kg, 160-350 mg/kg, 160-400 mg/kg, 160-450 mg/kg, 160-500 mg/kg, 180-200 mg/kg, 180-220 mg/kg, 180-240 mg/kg, 180-260 mg/kg, 180-280 mg/kg, 180-300 mg/kg, 180-350 mg/kg, 180-400 mg/kg, 180-450 mg/kg, 180-500 mg/kg, 200-220 mg/kg, 200-240 mg/kg, 200-260 mg/kg, 200-280 mg/kg, 200-300 mg/kg, 200-350 mg/kg, 200-400 mg/kg, 200-450 mg/kg, 200-500 mg/kg, 220-240 mg/kg, 220-260 mg/kg, 220-280 mg/kg, 220-300 mg/kg, 240-260 mg/kg, 240-280 mg/kg, 240-300 mg/kg, 240-350 mg/kg, 240-400 mg/kg, 240-450 mg/kg, 240-500 mg/kg, 260-280 mg/kg, 260-300 mg/kg, 280-300 mg/kg, 260-350 mg/kg, 260-400 mg/kg, 260-450 mg/kg, 260-500 mg/kg, 280-350 mg/kg, 280-400 mg/kg, 280-450 mg/kg, or 280-500 mg/kg.

In some embodiments, sequestering agent or a pharmaceutically acceptable salt thereof is adminstered at about at least 0.05 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 220 mg/kg, 230 mg/kg, 240 mg/kg, 250 mg/kg, 260 mg/kg, 270 mg/kg, 280 mg/kg, 290 mg/kg, 300 mg/kg, 350 mg/kg, 400 mg/kg, 450 mg/kg, or 500 mg/kg. In some embodiments, Compound A or a pharmaceutically acceptable salt thereof is administered at about less than 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 220 mg/kg, 230 mg/kg, 240 mg/kg, 250 mg/kg, 260 mg/kg, 270 mg/kg, 280 mg/kg, 290 mg/kg, 300 mg/kg, 350 mg/kg, 400 mg/kg, 450 mg/kg, or 500 mg/kg.

In some embodiments, the sequestering agent or a pharmaceutically acceptable salt thereof can be adminstered at about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, the CNS active agent is administered at about 0.1-1,000 μg/kg. In some embodiments, the CNS active agent is administered at about 1-1,000 μg/kg. In some embodiments, the CNS active agent is administered at about 1-500 μg/kg. In some embodiments, the opioid antagonist is adminstered at about 100-500 μg/kg. In some embodiments, the opioid antagonist is administered at about 100-150 μg/kg, 100-200 μg/kg, 100-250 μg/kg, 100-250 μg/kg, 100-300 μg/kg, 100-350 μg/kg, 100-400 μg/kg, 100-450 μg/kg, 100-500 μg/kg or 100-600 μg/kg. In some embodiments, the CNS active agent is administered at about at least 100 μg/kg, 150 μg/kg, 200 μg/kg, 250 μg/kg, 300 μg/kg, 350 μg/kg, or 400 μg/kg, 450 μg/kg, 500 μg/kg, 550 μg/kg, 600 μg/kg, 700 μg/kg, 800 μg/kg, 900 μg/kg, or 1,000 μg/kg. In some embodiments, the CNS active agent is administered at less than about 100 μg/kg, 150 μg/kg, 200 peg/kg, 250 μg/kg, 300 μg/kg, 350 μg/kg, 400 μg/kg, 450 μg/kg, 500 μg/kg, 550 μg/kg, 600 μg/kg, 700 μg/kg, 800 μg/kg, 900 μg/kg, or 1,000 μg/kg.

In some embodiments, the CNS active agent can be naloxone, ketamine, pentazocine, nalbuphine, buprenorphine, diprenorphine, methylnaltrexone, naltrexone, nalmefene, naloxegol, alvimopan, naldemedine, ketamine, benzodiazepine, an antihistamine, or a pharmaceutically acceptable salt thereof. In some embodiments, the CNS active agent can be an opioid receptor antagonist. In some embodiments the opioid receptor antagonist is naloxone. In some embodiments, the CNS active agent is atropine or scopolamine.

The disclosed embodiments can be formulated for various routes of administration, depending upon the particular carrier and other ingredients used. For example, the pharmaceutical compositions can be injected intramuscularly, subcutaneously, intradermally, or intravenously. They can also be administered via mucosa such as intranasally, intravaginally, intrarectally or orally. The compounds or compositions can also be administered topically through the skin via a transdermal patch, spot-on, pour-on or microneedles. Suspensions, solutions, powders, tablets, gel caps, etc., are contemplated herein.

Treatment of the drug intoxication or overdose can comprise repeated administration of the CNS active agent. In some embodiments, administration of the CNS active agent can comprise at least 0, 1, 2, 3, 4 or 5 doses over 8 hours. In some embodiments, administration of the CNS active agent can comprise about 0-5 doses, 0-4 doses, 0-3 doses, 0-2 doses, 0-1 doses, 1-5 doses, 1-4 doses, 1-3 doses, 1-2 doses, 2-3 doses, 2-4 doses, 2-5 doses, 3-4 doses, 3-5 doses, or 4-5 doses over 8 hours. In some embodiments, the administration of the CNS active agent can comprise at least 4 mg, 8 mg, 12 mg, or 16 mg over 8 hours. In some embodiments, the administration of the CNS active agent can comprise 4-8 mg, 4-12, 4-16 mg, 8-12 mg, 8-16 mg, 12-16 mg over 8 hours.

In some embodiments, the subject is a mammal. In some embodiments, the subject is a non-human primate. In some embodiments, the subject is a human.

Toxic Agents and Drugs of Abuse

In some embodiments, the present disclosure provides methods of treating or preventing intoxication of overdose, or a symptoms thereof, resulting from a toxic agent. In some embodiments, the toxic agent is a drug of abuse. In some embodiments, the toxic agent is selected from the group consisting of an opioid, a stimulant, a nerve agent, an allergen, and a metabolically or digestion derived toxicant.

The term “substance use disorder” as used in the present application refers to any stages associated with administration of, addiction to and withdrawal from a substance of abuse. This includes craving a substance, administering the substance and experiencing euphoria (a high), contentment or relaxation. When abstinent from the substance the subject may experience irritability, anxiety, sweating, nausea, vomiting, diarrhea, fatigue, tremors, headache, insomnia, loss of concentration, hallucinations, seizures and increased cravings. These are also known as withdrawal symptoms.

In some embodiments, the toxic agent is an opioid. In some embodiments, the opioid can be opium, fentanyl, carfentanil, hydrocodone, codeine, morphine, or any combination thereof. Overdose of opioids can be recognized through the appearance of pinpoint pupils, loss of consciousness, depressed heart rate, and difficulties breathing. Difficulty breathing results in lower oxygen levels. In addition, this can manifest in a subject as a lower respiration rate compared to an individual who does not have a opioid overdose.

In some embodiments, the toxic agent is a stimulant. A stimulant is a substance that raises levels of physiological or nervous activity in the body, which, at high doses, can lead to dangerously high body temperature, irregular heartbeat, heart failure, seizures, and death. In some embodiments, the stimulant can be caffeine, Ritalin, cocaine, amphetamines, crystal meth, methamphetamines, phencyclidine, cocaine, 3,4-methylenedioxy-methamphetamine (MDMA), and the like. Overdose of stimulants can be recognized through the appearance of excited delirium, increased excitedness, paranoia, psychosis, and elevated blood pressure. In some embodiments, the sequestration agent binds to the stimulant with a $K_a$ of at least about $1\times10^3 M^{-1}$, $1\times10^4 M^{-1}$, $1\times10^5 M^{-1}$, $1\times10^6 M^{-1}$, $1\times1\times10^7 M^{-1}$, $1\times10^8 M^{-1}$, or $1\times10^9 M^{-1}$.

In some embodiments, the toxic agent is a nerve agent. A nerve agent is a substance that inhibits cholinesterase and affect the nervous system. Examples include but are not limited to VX, sarin, soman, tabun, and organophosphate pesticides.

In some embodiments, the toxic agent is a metabolically and digestion-derived toxicant. A metabolically and/or digestion derived toxicant is a CNS active substance produced in excess in the process of human metabolic and digestive activity. Examples include but are not limited to: the excess of phenylalanine produced in the rare genetic metabolic disease Phenylketonuria and in hepatic encephalopathy, a liver dysfunction disorder, and the excess of cholesterol and fatty substances produced in Niemann-Pick disease.

Treatment of drug intoxication or overdose can comprise administration of a CNS active agent (e.g., opioid receptor antagonist) to relieve or ameliorate the recurring symptoms due to the drug of abuse. In some embodiments, the recurring symptoms can be associated with renarcotization.

Polydrug Associated Intoxication by a Drug of Abuse

In some embodiments, the intoxication by a drug of abuse can involve use of more than one drug, also known as a polydrug. In some embodiments, the polydrug associated intoxication can comprise an opioid and at least one other drug. In some embodiments, the polydrug associated intoxication can comprise a plurality of drugs of abuse. In some embodiments, the plurality of drugs of abuse comprise at least 1, at least 2, at least 3, at least 4, at least 5 drugs of abuse.

The drugs of abuse can be, but are not limited to, caffeine, alcohol, cocaine, an opioid, a stimulant, fentanyl, ketamine, heroin, amphetamines, crystal methamphetamine, CNS acting molecules, benzodiazepine, Adderall, Ritalin, sleeping pills, MDMA, or any combination thereof.

Binding Constants

In some embodiments, the sequestering agent is an acyclic cucurbituril such as Compound A. Table 1 tabulates exemplary binding constants of Compound A to toxic agents, as determined by $^{1}H$ NMR titrations between Compound A and a variety of compounds used in clinical practice. As will be apparent from the values in Table 1, the present figures and description, the binding affinity for compounds targeted for reversal is high.

TABLE 1

Binding constants ($K_a$) for Compound A

| Compound | Compound A $K_a$ ($\times 10^6 M^{-1}$) |
|---|---|
| Carfentanil | 2 |
| sufentanil** | 7.1 |
| fentanyl | 5 |
| furanyl fentanyl*** | 3 |
| acetyl fentanyl | 5.7 |
| Remifentanil | 0.03 |
| Methamphetamine | 1.9 |
| Amphetamine | 2 |
| buprenorphine** | 5.2 |
| naloxone** | 0.23 |
| Bradykinin | 0.001 |
| Histamine | 0.001 |
| Diphenhydramine | 0.004 |
| Promethazine | 0.003 |
| Dopamine | 0.25 |
| Phenylalanine | 0.009 |
| Epinephrine | 0.004 |
| Atropine | 0.05 |
| Scopolamine | 0.02 |
| midazolam* | 0.4 |
| diazepam* | <.001 |

In some embodiments, the sequestering agent is a pillararene, represented by the structure of Compound B or any derivatives thereof, wherein Compound B comprises the following structure:

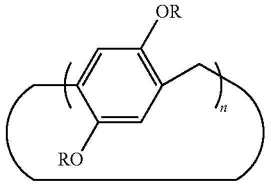

wherein n is 5-8, and R=$SO_3H$, or $SO_3Na$. In some embodiments, n is 6.

Table 2 tabulates exemplary binding constants of Compound B to toxic agents, as determined by $^{1}H$ NMR titrations between Compound B and a variety of compounds used in clinical practice. As will be apparent from the values in Table 2, the present figures and description, the binding affinity for compounds targeted for reversal is high.

TABLE 2

Binding constants ($K_a$) for compounds with Formula B

| Compound | Compound B $K_a$ ($\times 10^6 M^{-1}$) |
|---|---|
| methamphetamine | 8 |
| fentanyl citrate | 60 |
| Remifentanil | 0.8 |
| sufentanil citrate** | 40 |
| buprenorphine** | 0.6 |
| amphetamine | 4 |

**pH 6.15

In some embodiments, the sequestering agent is a cyclic cucurbituril such as Compound C or any derivatives thereof, wherein Compound C comprises the following structure:

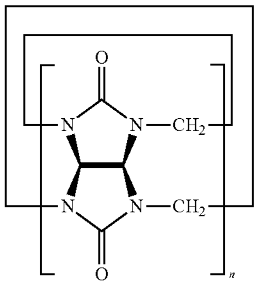

wherein n is 5, 6, 7 or 8, e.g., n=7.

Table 3 tabulates exemplary binding constants of Compound C to toxic agents, as determined by $^{1}H$ NMR titrations between Compound C and a variety of compounds used in clinical practice. As will be apparent from the values in Table 3, the present figures and description, the binding affinity for compounds targeted for reversal is high.

TABLE 3

Binding constants ($K_a$) for compounds with Formula C

| Compound | Compound C $K_a$ ($\times 10^6 M^{-1}$) |
|---|---|
| methamphetamine | 6 |
| fentanyl citrate | 10 |
| amphetamine | 5 |

Kits

In some embodiments, the disclosure provides kits that include a composition (e.g., a pharmaceutical composition) of the disclosure (e.g., a composition including a sequestration agent and CNS active agent). The kits can include instructions to allow a clinician (e.g., a physician or nurse) to administer the composition contained therein to a subject to treat narcotic intoxication and associated symptoms.

In certain embodiments, the kits include a package of a single-dose pharmaceutical composition(s) containing a therapeutically effective amount of the composition comprising the sequestration agent and CNS active agent of the disclosure. Optionally, instruments or devices necessary for administering the pharmaceutical composition(s) may be included in the kits. For instance, a kit of this disclosure may provide one or more pre-filled syringes containing a therapeutically effective amount of the composition of the disclosure. Furthermore, the kits may also include additional components such as instructions regarding administration schedules for a subject having narcotic intoxication and associated symptoms.

In some embodiments, the compound or compositions can be provided in unit dosage form in a suitable container. The term “unit dosage form” refers to a physically discrete unit suitable as a unitary dosage for human or animal use. Each unit dosage form may contain a predetermined amount of the inventive compound (and/or other active agents) in the carrier calculated to produce a desired effect. In other embodiments, the compound can be provided separate from the carrier (e.g., in its own vial, ampule, sachet, or other suitable container) for on-site mixing before administration to a subject. A kit comprising the compound(s) is also disclosed herein. The kit further comprises instructions for administering the compound to a subject. The compound(s) can be provided as part of a dosage unit, already dispersed in a pharmaceutically-acceptable carrier, or it can be provided separately from the carrier. The kit can further comprise instructions for preparing the compounds for administration to a subject, including for example, instructions for dispersing the compounds in a suitable carrier.

In some embodiments, the sequestration agent and the CNS active agent can be in the same formulation. In some embodiments, the sequestration and the CNS active agent can be in the different formulations.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study.

Pharmaceutical Compositions

The composition of this disclosure, can, in some embodiments, be included in compositions (e.g., pharmaceutical compositions). The pharmaceutical compositions of the disclosure may further include a pharmaceutically acceptable carrier, excipient, or diluent.

The term “pharmaceutical composition” as used herein refers to a composition containing a sequestering agent and a CNS active agent described herein formulated with a pharmaceutically acceptable carrier, and manufactured or sold with the approval of a governmental regulatory agency as part of a therapeutic regimen for the treatment of disorder in a mammal. Pharmaceutical compositions can be formulated, for example, for oral administration in unit dosage form (e.g., a tablet, capsule, caplet, gel cap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

The term “pharmaceutically acceptable carrier” as used herein refers to a carrier which is physiologically acceptable to a treated mammal (e.g., a human) while retaining the therapeutic properties of the protein with which it is administered. One exemplary pharmaceutically acceptable carrier is physiological saline. Other physiologically acceptable carriers and their formulations are known to one skilled in the art and described, for example, in Remington’s Pharmaceutical Sciences ($18^{th}$ edition, A. Gennaro, 1990, Mack Publishing Company, Easton, PA), incorporated herein by reference.

Pharmaceutical compositions containing sequestering agent and a CNS active agent, are, in some embodiments, prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof.

A pharmaceutically acceptable excipient is, in some examples, an excipient described in the Handbook of Pharmaceutical Excipients, American Pharmaceutical Association (1986). Non-limiting examples of suitable excipients include a buffering agent, a preservative, a stabilizer, a binder, a compaction agent, a lubricant, a chelator, a dispersion enhancer, a disintegration agent, a flavoring agent, a sweetener, a coloring agent.

In some embodiments an excipient is a buffering agent. Non-limiting examples of suitable buffering agents include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium gluconate, aluminum hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof is used, in some embodiments, in a pharmaceutical composition of the present disclosure.

In some embodiments an excipient comprises a preservative. Non-limiting examples of suitable preservatives include antioxidants, such as alpha-tocopherol and ascorbate, and antimicrobials, such as parabens, chlorobutanol, and phenol. In some examples, antioxidants further include but are not limited to EDTA, citric acid, ascorbic acid, butylated hydroxytoluene (BHT), butylated hydroxy anisole (BHA), sodium sulfite, p-amino benzoic acid, glutathione, propyl gallate, cysteine, methionine, ethanol and N-acetyl cysteine. In some instances preservatives include validamycin A, TL-3, sodium ortho vanadate, sodium fluoride, N-a-tosyl-Phe-chloromethylketone, N-a-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In some embodiments a pharmaceutical composition as described herein comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof. The binders used in a pharmaceutical formulation are, in some examples, selected from starches such as potato starch, corn starch, wheat starch; sugars such as sucrose, glucose, dextrose, lactose, maltodextrin; natural and synthetic gums; gelatine; cellulose derivatives such as microcrystalline cellulose, hydroxypropyl cellulose, hydroxyethyl cellulose, hydroxypropyl methyl cellulose, carboxymethyl cellulose, methyl cellulose, ethyl cellulose; polyvinylpyrrolidone (povidone); polyethylene glycol (PEG); waxes; calcium carbonate; calcium phosphate; alcohols such as sorbitol, xylitol, mannitol and water or any combinations thereof.

In some embodiments a pharmaceutical composition as described herein comprises a lubricant as an excipient.

Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricants that are used in a pharmaceutical formulation, in some embodiments, are be selected from metallic stearates (such as magnesium stearate, calcium stearate, aluminum stearate), fatty acid esters (such as sodium stearyl fumarate), fatty acids (such as stearic acid), fatty alcohols, glyceryl behenate, mineral oil, paraffins, hydrogenated vegetable oils, leucine, polyethylene glycols (PEG), metallic lauryl sulphates (such as sodium lauryl sulphate, magnesium lauryl sulphate), sodium chloride, sodium benzoate, sodium acetate and talc or a combination thereof.

In some embodiments a pharmaceutical formulation comprises a dispersion enhancer as an excipient. Non-limiting examples of suitable dispersants include, in some examples, starch, alginic acid, polyvinylpyrrolidones, guar gum, kaolin, bentonite, purified wood cellulose, sodium starch glycolate, isomorphous silicate, and microcrystalline cellulose as high HLB emulsifier surfactants.

In some embodiments a pharmaceutical composition as described herein comprises a disintegrant as an excipient. In some embodiments a disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments a disintegrant is an effervescent disintegrant. Non-limiting examples of suitable effervescent disintegrants include sodium bicarbonate in combination with citric acid, and sodium bicarbonate in combination with tartaric acid.

In some embodiments an excipient comprises a flavoring agent. Flavoring agents incorporated into an outer layer are, in some examples, chosen from synthetic flavor oils and flavoring aromatics; natural oils; extracts from plants, leaves, flowers, and fruits; and combinations thereof. In some embodiments a flavoring agent can be selected from the group consisting of cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments an excipient comprises a sweetener. Non-limiting examples of suitable sweeteners include glucose (corn syrup), dextrose, invert sugar, fructose, and mixtures thereof (when not used as a carrier); saccharin and its various salts such as a sodium salt; dipeptide sweeteners such as aspartame; dihydrochalcone compounds, glycyrrhizin; *Stevia rebaudiana* (Stevioside); chloro derivatives of sucrose such as sucralose; and sugar alcohols such as sorbitol, mannitol, sylitol, and the like.

In some instances, a pharmaceutical composition as described herein comprises a coloring agent. Non-limiting examples of suitable coloring agents include food, drug and cosmetic colors (FD & C), drug and cosmetic colors (D & C), and external drug and cosmetic colors (Ext. D & C). A coloring agents can be used as dyes or their corresponding lakes.

In some instances, a pharmaceutical composition as described herein comprises a chelator. In some cases, a chelator is a fungicidal chelator. Examples include, but are not limited to: ethylenediamine-N,N,N',N'-tetraacetic acid (EDTA); a disodium, trisodium, tetrasodium, dipotassium, tripotassium, dilithium and diammonium salt of EDTA; a barium, calcium, cobalt, copper, dysprosium, europium, iron, indium, lanthanum, magnesium, manganese, nickel, samarium, strontium, or zinc chelate of EDTA; trans-1,2-diaminocyclohexane-N,N,N',N'-tetraacetic acid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis (methylenephosphonic acid) hemihydrate; N-(2-hydroxyethyl)ethylenediamine-N,N',N'-triacetic acid; ethylenediamine-N,N,N',N'-tetrakis(methylenephosphonic acid); 0,0'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphonic acid); 7,19,30-trioxa-1,4,10,13,16,22,27,33-octaazabicyclo[11,11,11]pentatriacontane hexahydrobromide; or triethylenetetramine-N,N,N',N",N'",N'"-hexaacetic acid.

Also contemplated are combination products that include an sequestering agent and opioid antagonist as disclosed herein and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, posaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that a peptide can be combined with topical antifungal agents such as ciclopirox olamine, haloprogin, tolnaftate, undecylenate, topical nystatin, amorolfine, butenafine, naftifine, terbinafine, and other topical agents. In some instances, a pharmaceutical composition comprises an additional agent. In some cases, an additional agent is present in a therapeutically effective amount in a pharmaceutical composition.

Under ordinary conditions of storage and use, the pharmaceutical compositions as described herein comprise a preservative to prevent the growth of microorganisms. In certain examples, the pharmaceutical compositions as described herein do not comprise a preservative. The pharmaceutical forms suitable for injectable use include sterile aqueous solutions or dispersions and sterile powders for the extemporaneous preparation of sterile injectable solutions or dispersions. The pharmaceutical compositions comprise a carrier which is a solvent or a dispersion medium containing, for example, water, ethanol, polyol (e.g., glycerol, propylene glycol, and liquid polyethylene glycol, and the like), and/or vegetable oils, or any combinations thereof. Proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, isotonic agents are included, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the liquid dosage form is suitably buffered if necessary and the liquid diluent rendered isotonic with sufficient saline or glucose. The liquid dosage forms are especially suitable for intravenous, intramuscular, subcutaneous, and intraperitoneal administration. In this connection, sterile aqueous media that can be employed will be known to those of skill in the art in light of the present disclosure. For example, one dosage is dissolved, in certain cases, in 1 mL to 20 mL of isotonic NaCl solution and either added to 100 mL to 1000 mL of a fluid, e.g., sodium-bicarbonate buffered saline, or injected at the proposed site of infusion.

In certain embodiments, sterile injectable solutions are prepared by incorporating a immunotherapy agent, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. The compositions disclosed herein are, in some instances, formulated in a neutral or salt form. Pharmaceutically-acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups are, in some cases, derived from inorganic bases such as, for example, sodium, potassium, ammonium, calcium, or ferric hydroxides, and such organic bases as isopropylamine, trimethylamine, histidine, procaine and the like. Upon formulation, the pharmaceutical compositions are administered, in some embodiments, in a manner compatible with the dosage formulation and in such amount as is therapeutically effective.

In certain embodiments, a pharmaceutical composition of this disclosure comprises an effective amount of a sequestering agent and a CNS active agent, as disclosed herein, combined with a pharmaceutically acceptable carrier. "Pharmaceutically acceptable," as used herein, includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically compatible carriers can include gels, bioabsorbable matrix materials, implantation elements containing the immunotherapeutic agents or any other suitable vehicle, delivery or dispensing means or material. Such carriers are formulated, for example, by conventional methods and administered to the subject at an effective amount.

EXAMPLES

Example 1: Assessment of a Combination of Naloxone and a Sequestration Agent for the Resolution of Narcotic Intoxication and Mitigation of Renarcotization African green monkeys (AGMs; n=8) were exposed to 15 μg/kg (sc) carfentanil. Naloxone (355.12 μg/kg, im) was administered at loss of posture or <10 breaths per minute (bpm) followed immediately with Compound A (100 or 200 mg/kg, im). A second dose of naloxone (355.12 μg/kg, im) was administered within approximately 3 minutes if respiration rate was ≤10 bpm or respiration quality was declining.

The average latency to naloxone administration is presented in the table below. Initial treatment with Compound A (100 mg/kg) and naloxone was sufficient in 3/8 (number responding/total number) to attenuate carfentanil-induced respiratory depression for the duration of the experiment. Respiratory rates at the end of testing were between 15 and 20 breaths per minute (bpm) for three AGMs that did not require additional naloxone at the end of testing. The remaining five AGMs required a second naloxone dose). One AGM remained apneic after the initial dose of naloxone and required a second naloxone dose that was administered within three minutes of the initial treatment. Additional naloxone beyond the second dose was not required. The other four were ataxic with shallow erratic breaths of about or below 12 bpm. In contrast, none of the AGMs administered 200 mg/kg Compound A required an additional naloxone dose at the end of the day, and respiratory rates at the end of the day were mostly normal (16-24 bpm) with the exception of one AGM with a steady rate of 14 bpm. In the 200 mg/kg group, only one AGM failed to respond to the initial dose of naloxone and was administered another dose 3 minutes later.

TABLE 4

| Latency to Treatment (minutes) | | | | |
|---|---|---|---|---|
| Group | Naloxone #1 | Naloxone #2 | Naloxone #3 | Naloxone #4 |
| 0 mg/kg Compound A | 12 ± 6 (6/6) | 155 ± 50 (6/6) | 278 ± 104 (4/6) | 339 (1/6) |
| 100 mg/kg Compound A | 11 ± 4 (8/8) | 250 ± 4 (5/8)* | N/A (0/0) | N/A (0/0) |
| 200 mg/kg Compound A | 13 ± 4 (8/8) | 14 (1/8)* | N/A (0/0) | N/A (0/0) |

*One study subject in each of the 100 mg/kg and 200 mg/kg groups required an additional dose of naloxone within 3 minutes after failing to respond to the initial treatment. In both cases further naloxone treatment was not required for the duration of the experiment.

The majority of AGMs (5/8) administered 100 mg/kg Compound A after exposure consumed some or all of daily enrichment and/or biscuits by the end of the day. The remaining AGMs each wasted 39% of the daily biscuit allotment. Biscuit waste (22%) was evident in only one of eight AGMs when treated with 200 mg/kg Compound A. In contrast, most AGMs exposed to carfentanil and treated with naloxone show little if any interest in food. In a previous study, four of five male AGMs exposed to 15 μg/kg carfentanil and treated with naloxone wasted ≥50% of allotted biscuits.

In a safety assessment, both Compound A and the combination of Compound A and naloxone were well tolerated by all study subjects.

Figure 2:
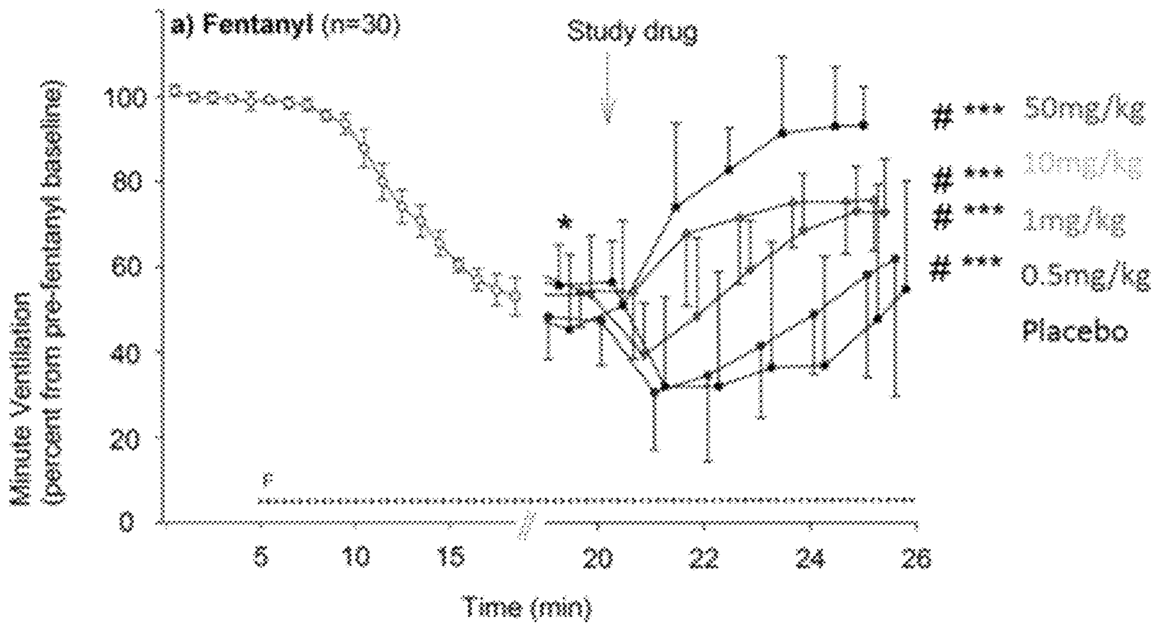
FIG. 2 shows the treatment of fentanyl-induced respiration depression using Compound A in a dose-dependent treatment regimen. Fentanyl is administered and Compound A is administered around 12-15 minutes later. Compound A is provided at various concentrations: 0.5 mg/kg, 1 mg/kg, 10 mg/kg, and 50 mg/kg. (T. Thevathasnan et. Al., British Journal of Anasthesia, 2020).

Example 2: Dose Dependent Treatment Using Compound a for Fentanyl-Induced Respiration Depression In this study, 30 rats were administered fentanyl and administered Compound A intramuscularly approximately 12-15 minutes after the initiation of fentanyl infusion. At 12-15 minutes, minute ventilation (percent from pre-fentanyl baseline) was significantly lower than the base line (*:p<0.001). In the Compound A treatment dosing schemes, each dosing scheme was provided significant improvement in minute ventilation compared to the preceding lower dose of Compound A (#:p<0.001) (FIG. 2)

Example 3: Evaluation of Compound A Treatment of Carfentanil and Methamphetamine Intoxication African green monkeys (AGMs) are exposed to 15 μg/kg (sc) carfentanil and methamphetamine and administered naloxone and Compound A. For example, naloxone (355.12 μg/kg, im) is administered at loss of posture or <10 breaths per minute (bpm) and is followed immediately with Compound A (100 or 200 mg/kg, im). A second dose of naloxone (355.12 μg/kg, im) is administered within approximately 3 minutes if respiration rate is ≤10 bpm or respiration quality is declining.

For example, initial treatment with Compound A (100 mg/kg or 200 mg/kg) and naloxone may be sufficient to attenuate carfentanil/methamphetamine induced respiratory depression. If loss of posture or depressed respiratory rate is observed, another dose naloxone is administered. If no loss of posture or depressed respiratory rate is observed, then no naloxone is administered to the AGM. In addition, loss of appetite is monitored to determine if appetite can be restored after treatment.

Example 4: Determination of Renal Clearance of Compound A Sequestered Compounds

To determine the efficacy of Compound A sequestering of the tested compounds lead to reduction of a compound in the bloodstream.

For example, African green monkeys (AGMs) are exposed to of different opioids, stimulants, and narcotics. Naloxone (355.12 μg/kg, im) is administered at loss of posture or <10 breaths per minute (bpm) followed immediately with Compound A (100 or 200 mg/kg, im). A second dose of naloxone (355.12 μg/kg, im) is administered within approximately 3 minutes if respiration rate was ≤10 bpm or respiration quality was declining. During the course of the treatment and after the treatment, urine is collected and analyzed to determine if an increase of Compound A-bound compounds are excreted.

Example 5: Dose Dependent Treatment Using Coformulation of Compound A and Naloxone Sprague-Dawley rats were administered 20 μg/kg of carfentanil vi IV, immediately followed by a coformulation of Compound A (400 mg/kg) and naloxone (0.5 mg/kg) via IM injection.

The coformulation of Compound A and naloxone was prepared by weighing out the appropriate amount of naloxone and Compound A and dissolving in 90% of the desired volume of water for injection (WFI). Vortex for 1 minute or until a clear solution is achieved. Adjust pH to pH 7-8 if necessary. Q.s. to final volume with WFI.

The coformulation of Compound A and naloxone rapidly sequestered the carfentanil in the plasma, significantly lowering the level of carfentanil in the plasma in the rats receiving the coformulation compared to the level of carfentanil in the rats receiving the saline control.

Figure 3:
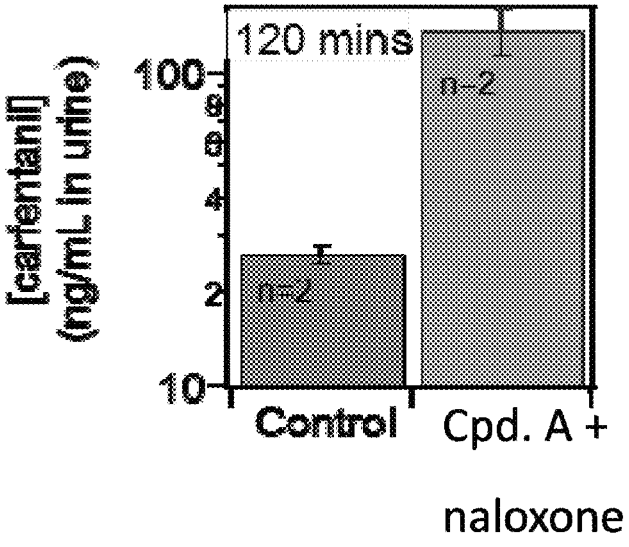
FIG. 3 shows urine concentration of carfentanil at 120 minutes after administration of carfentanil (IV, 20 μg/kg) followed immediately by either saline control or formulation (IM, 400 mg/kg Compound A and 0.5 mg/kg naloxone).

FIG. 3 shows the urine concentration of carfentanil at 120 minutes after administration of carfentanil (IV, 20 μg/kg) followed immediately by either saline control or formulation (IM, 400 mg/kg Compound A and 0.5 mg/kg naloxone). Animals treated with the formulation demonstrate a ~5-fold increased clearance of carfentanil into urine versus saline control. Error bars indicate maximum and minimum values for each group.

In addition, the coformulation reverses Loss of Righting Reflex (LORR) in 14 minutes versus 60 minutes for saline. Further, the coformulation restores respiration in 5 min. Table 5 below shows breaths per minute after 20 ug/kg carfentanil followed immediately by formulation of 400 mg/kg Compound A and 0.5 mg/kg naloxone.

TABLE 5

| Time after Coformulation (minutes) | Breaths per minute | Percent Recovery |
|---|---|---|
| 1 | 37 | 31% |
| 3 | 77 | 65% |
| 4 | 88 | 75% |
| 5 | 118 | 100% |

Breaths per minute were calculated based on manual counting of chest contractions from high quality videos of the rats after administration of the formulation.

It should be noted that 0.5 mg/kg naloxone, converted to Human Equivalent Dose (HED) is 0.081 mg/kg or 5.6 mg for 70 kg human.

Carfentanil is a synthetic opioid approximately 10,000 times more potent than morphine and 100 times more potent than fentanyl. The estimated lethal dose of fentanyl in humans is 2 mg. A shortcoming of opioid receptor antagonists is re-narcotization after initial treatment, thereby necessitating repeat administration. Long-standing advisories from CDC and other federal and state authorities have cautioned that multiple doses of naloxone may need to be administered per overdose event because of fentanyl's increased potency relative to other opioids.

The combination and method of the present disclosure provides therapeutically effective treatment of carfentanil intoxication without requiring the administration substantially higher amounts of naloxone (than required to treat fentanyl intoxication) and without requiring repeated administration of naloxone to prevent re-narcotization. Thus, the results demonstrate that (1) a sequestrant described herein (e.g., Compound A) was able to rapidly sequester and clear a toxic agent (e.g., an opioid such as Carfentanil); and that (2) a CNS active agent (e.g., naloxone) was effective at binding to the opioid receptor and displacing the toxic agent, without the need for multiple administrations.

The data described herein demonstrates that the described method of administering Compound A and naloxone, when administered in as Example 1 or in coformulation as in Example 5, rapidly restores respiration, reverses LORR, reduces the level of opioid in the plasma, increases the clearance of opioid into the urine, and reduces re-narcotization. This is effective across a broad range of CNS active agents and a broad range of coformulation ratios.

Example 6: Co-Formulation of Naloxone and Compound A

Figure 4:
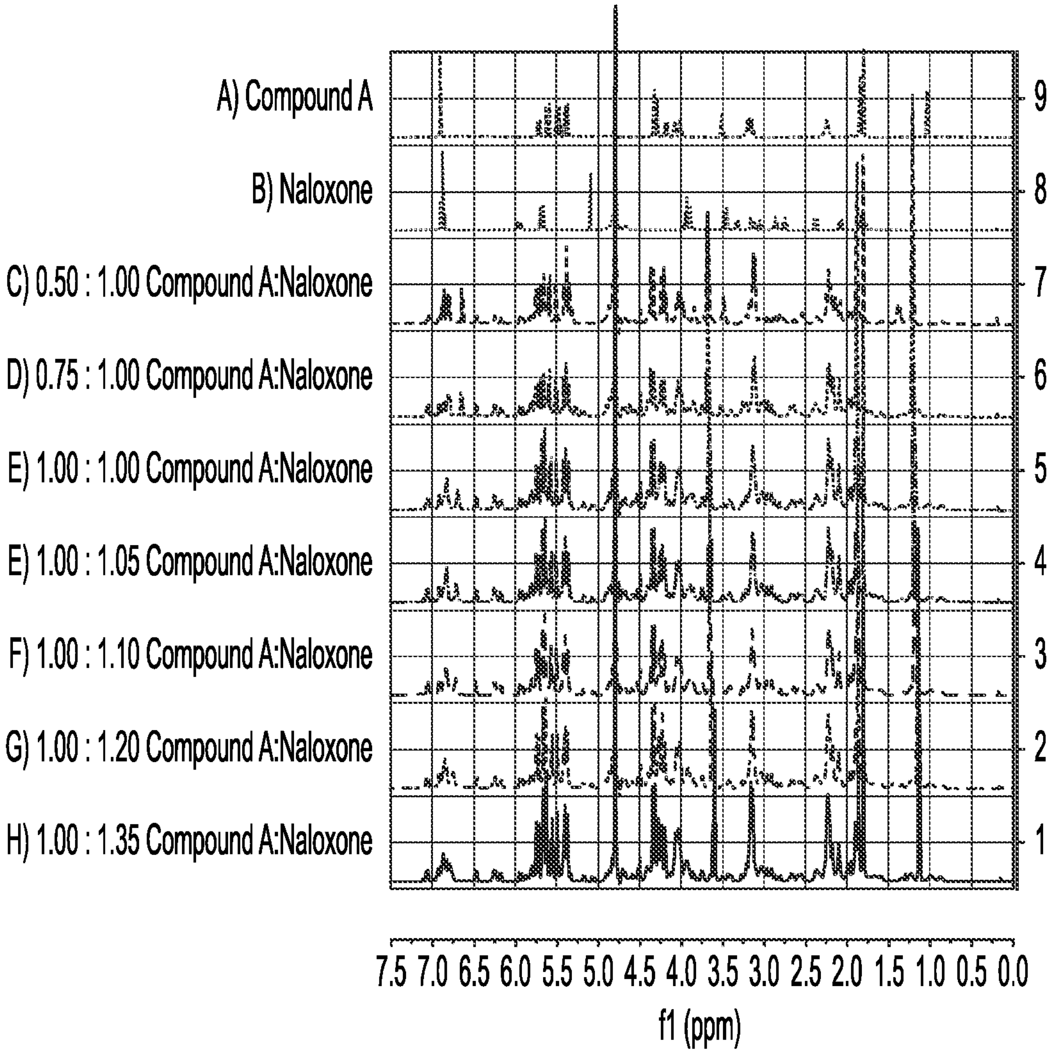
FIG. 4 shows analysis of $^1H$ NMR spectra of Compound A and naloxone, prepared in $D_2O$ with molar ratios of 1:0, 0:1, 0.5:1, and 1:1 respectively.

Samples of Compound A and naloxone were prepared in $D_2O$ with molar ratios of, 1:0, 0:1, 0.5:1, 0.75:1, 1:1, 1:1.05, 1:1.10, 1:1.2, and 1:1.35 respectively. Analysis of the $^1H$ NMR spectra of these samples (FIG. 4) shows that Compound A is binding naloxone. Firstly, the singlet corresponding to the aromatic protons of Compound A becomes asymmetrical when naloxone is added (spectra C, D). Additionally, several significant chemical shift changes occur. The naloxone singlet at δ 5.09 (spectrum B) is not visible when Compound A is added (spectra C and D) and has likely shifted upfield where it would be obscured by the water signal. Likewise, the signals from naloxone's vinyl protons (δ 5.96, 5.68) are shifted after addition of Compound A indicating that binding has occurred. Further addition of Compound A, after a 1:1 ratio of Compound A to naloxone is reached, does not significantly change the NMR spectra obtained, which indicates that no significant change in the binding can be observed beyond this point using $^1H$ NMR.

Embodiments

Embodiment 1. A pharmaceutical composition for treating intoxication, overdose, or symptoms thereof due to use of at least one drug of abuse in a human comprising:

i) a sequestration agent or a pharmaceutically acceptable salt thereof;
ii) a central nervous system (CNS) active agent or a pharmaceutically acceptable salt thereof; and
iii) a pharmaceutically acceptable excipient;

wherein the sequestration agent is selected from a cyclic or acyclic cucurbituril or pillararene.

Embodiment 2. A pharmaceutical composition for treating intoxication due to use of at least one drug of abuse or symptoms thereof comprising:

i) a sequestration agent or a pharmaceutically acceptable salt thereof in an amount sufficient to sequester the at least one toxic agent; and
ii) a central nervous system (CNS) active agent or a pharmaceutically acceptable salt thereof;

wherein the sequestration agent is selected from a cucurbituril, pillararene, cyclodextrin or calixarene.

Embodiment 3. A pharmaceutical composition for treating intoxication due to use of at least one drug of abuse or symptoms thereof comprising:

i) a sequestration agent or a pharmaceutically acceptable salt thereof in an amount sufficient to sequester the at least one toxic agent; and
ii) a central nervous system (CNS) active agent or a pharmaceutically acceptable salt thereof.

Embodiment 4. The pharmaceutical composition of any one of embodiments 1-3, wherein the sequestration agent and CNS active agent are in the same formulation.

Embodiment 5. The pharmaceutical composition of any one of embodiments 1-3, wherein the sequestration agent and CNS active agent are in different formulations.

Embodiment 6. The pharmaceutical composition of any one of embodiments 1-5, wherein the CNS active agent is selected form the group consisting of: naloxone, pentazocine, nalbuphine, diprenorphine, methylnaltrexone, naloxegol, alvimopan, naltrexone, nalmefene, buprenorphine, or a pharmaceutically acceptable salt thereof.

Embodiment 7. The pharmaceutical composition of embodiment 6, wherein the CNS active agent is naloxone.

Embodiment 8. The pharmaceutical composition of embodiments 1-7, wherein the sequestration agent is a cyclic or acyclic cucurbituril.

Embodiment 9. The pharmaceutical composition of embodiment 8, wherein the cucurbituril is Compound A or any derivatives thereof, wherein Compound A comprises the following structure:

Compound A

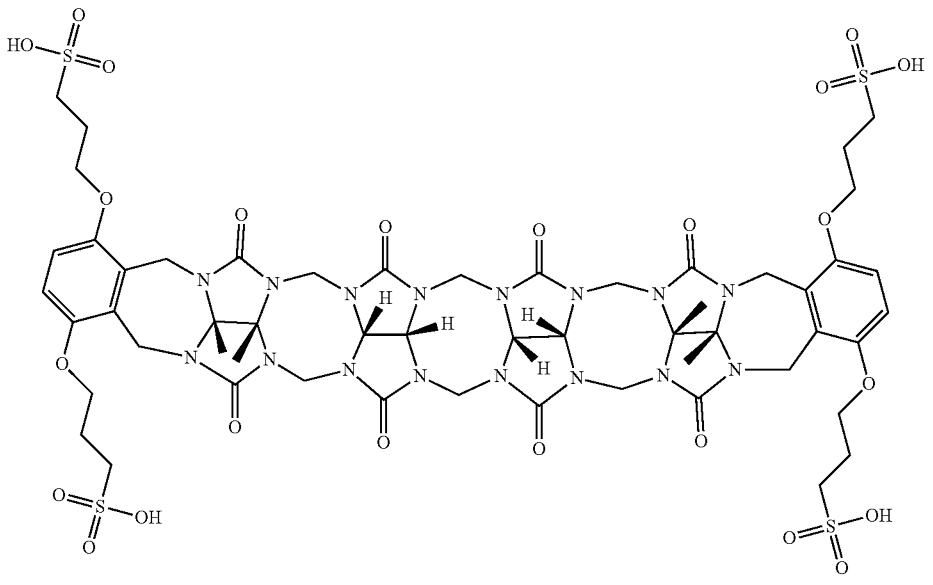

Embodiment 10. The pharmaceutical composition of embodiment 9, wherein the Compound A or a pharmaceutically acceptable salt thereof is present at about 10 mg/kg to 300 mg/kg.

Embodiment 11. The pharmaceutical composition of embodiment 7 or 8, wherein naloxone or a pharmaceutically acceptable salt thereof is present at about 100-400 μg/kg.

Embodiment 12. The pharmaceutical composition of any one of embodiments 1-9, wherein the sequestration agent binds to an opioid with a $K_a$ of at least about $1\times10^5 M^{-1}$, $1\times10^6 M^{-1}$, $1\times10^7 M^{-1}$, or $1\times10^8 M^{-1}$.

Embodiment 13. The composition of any one of embodiments 1-9, wherein the sequestration agent binds to a stimulant with a $K_a$ of at least about $1\times10^5 M^{-1}$, $1\times10^6 M^{-1}$, $1\times10^7 M^{-1}$, or $1\times10^8 M^{-1}$.

Embodiment 14. The pharmaceutical composition of embodiment 12, wherein the opioid is selected a group consisting of fentanyl, fentanyl analogs, carfentanil, acetylfentanyl, alfentanil, and any combinations thereof.

Embodiment 15. The pharmaceutical composition of embodiment 13, wherein the stimulant is selected from the group consisting of amphetamines, methamphetamine, Ritalin, phencyclidine, cocaine, MDMA, and any combination thereof.

Embodiment 16. A method of treating a suspected opioid overdose or symptom thereof in a human, the method comprising:

administering a therapeutically effective amount of a sequestration agent co-administered with a therapeutically effective amount of a central nervous system (CNS) active agent, wherein the administration is effective to treat the suspected opioid overdose in the human in need thereof.

Embodiment 17. The method of embodiment 16, wherein the opioid is selected from a group consisting of fentanyl, fentanyl analogs, carfentanil, heroin, morphine acetylfentanyl, alfentanil, and any combinations thereof.

Embodiment 18. A method of treating an intoxication of a drug of abuse or symptom thereof in a human, the method comprising:

co-administering a therapeutically effective amount of a sequestration agent with a therapeutically effective amount of a central nervous system (CNS) active agent, wherein the administration is effective to treat the stimulant overdose or symptom thereof in the human in need thereof.

Embodiment 19. The method of embodiment 18, wherein the stimulant is selected from a group consisting of amphetamines, methamphetamine, Ritalin, cocaine, caffein, phencyclidine, MDMA, and any combinations thereof.

Embodiment 20. A method of treating a suspected overdose or symptom thereof in a subject, comprising co-administering a therapeutically effective amount of a sequestration agent with a therapeutically effective amount of a central nervous system (CNS) active agent, wherein the subject has a suspected overdose from a plurality of drugs of abuse.

Embodiment 21. The method of embodiment 20, wherein the plurality of drugs comprises at least 1, at least 2, at least 3, at least 4 drugs of abuse.

Embodiment 22. The method of embodiment 20-21, wherein the drugs of abuse comprises an opioid or stimulant.

Embodiment 23. The method of embodiment 22, wherein the opioid is selected from a group consisting of fentanyl, carfentanil, fentanyl analogs, fentanyl derivatives, heroin, morphine, acetylfentanyl, alfentanil, and any combinations thereof and wherein the stimulant is selected from the group consisting of amphetamines, methamphetamine, Ritalin, phencyclidine, cocaine and MDMA.

Embodiment 24. The method of any one of embodiments 16-23, wherein the sequestration agent is administered before the CNS active agent.

Embodiment 25. The method of any one of embodiments 16-23, wherein the sequestration agent is administered after the CNS active agent.

Embodiment 26. The method of embodiment 16-25, wherein the CNS active agent is administered less than 5 minutes, 4 minutes, 3 minutes, 2 minutes, or 1 minute after the sequestration agent.

Embodiment 27. The method of embodiment 16-25, wherein the sequestration agent is administered less than 5 minutes, 4 minutes, 3 minutes, 2 minutes, or 1 minute after the CNS active agent.

Embodiment 28. The method of any one of embodiments 16-27, further comprising administration of the CNS active agent.

Embodiment 29. The method of any one of embodiments 16-28, wherein the method is administered intramuscularly, intranasally, sublingually, buccally, or intravenously.

Embodiment 30. The method of any one of embodiments 16-29, wherein the subject is a human.

Embodiment 31. The method of embodiment 30, further comprising monitoring the subject to determine whether subsequent administration of a CNS active agent is needed.

Embodiment 32. The method of embodiment 31, wherein the monitoring comprises measuring the subject for abnormal heartrate, respiratory rate, appetite, cognitive capacity, or any combination thereof.

Embodiment 33. The method of embodiment 32, further comprising administration of naloxone after the monitoring.

Embodiment 34. The method of any one of embodiments 1-33, wherein the method provides alleviation of an opioid overdose, stimulant overdose, or a symptom thereof.

Embodiment 35. The method of embodiment 34, wherein alleviation of an opioid overdose, stimulant overdose, comprises restoration of normal respiration rate.

Embodiment 36. The method of embodiment 35, wherein normal respiration rate comprises at least about 15 to 20 breaths per minute.

Embodiment 37. The method of embodiment 34, wherein the alleviation of narcotic intoxication comprises restoration of appetite.

Embodiment 38. The method of embodiment 34, wherein alleviation of narcotic intoxication prevents renarcotization.

Embodiment 39. The method of any one of embodiments 16-38, wherein the sequestration agent or a pharmaceutically acceptable salt thereof is administered at about 10 mg/kg to 300 mg/kg.

Embodiment 40. The method of any one of embodiments 16-39, wherein the CNS active agent or a pharmaceutically acceptable salt thereof is administered at about 100-400 μg/kg.

Embodiment 41. The method of any one of embodiments 16-40, wherein the sequestration agent comprises Compound A, or any derivative thereof.

Embodiment 42. The method of any one of embodiments 16-41, wherein the CNS active agent comprises naloxone or a pharmaceutically acceptable salt thereof.

Embodiment 43. The method of any one of embodiments 16-42, further comprising administration of the CNS active agent.

Embodiment 44. The method of embodiment 43, wherein the administration of the CNS active agent comprises at least about 1, 2, 3, or 4 doses over 8 hours.

Embodiment 45. The method of embodiment 43, wherein the administration of the CNS active agent comprise at least about 4 mg, 8 mg, 12 mg, or 16 mg over 8 hours.

Embodiment 46. A kit compromising a composition, the composition comprising:

i) a therapeutically effective amount of a central nervous system (CNS) active agent; and ii) a therapeutically effective amount of a sequestration agent;

wherein the kit provides instructions to administer the composition to a subject in need thereof.

Embodiment 47. The kit of embodiment 46, wherein the sequestration agent and the CNS active agent are in the same formulation.

Embodiment 48. The kit of embodiment [0217], wherein the sequestration agent and the CNS active agent are in different formulations.

Embodiment 49. The kit of any one of embodiments 46-48, wherein the sequestration agent or a pharmaceutically acceptable salt thereof is administered at about 10 mg/kg to 300 mg/kg to the subject in need thereof.

Embodiment 50. The kit of embodiment 49, wherein the sequestration agent is Compound A or any derivative thereof.

Embodiment 51. The kit of any one of embodiments 46-48, wherein the CNS active agent or a pharmaceutically acceptable salt thereof is administered at about 100-400 μg/kg to a subject in need thereof.

Embodiment 52. The kit of embodiment 51, wherein the CNS active agent is naloxone.

Embodiment 53. The kit of embodiment 46, wherein the subject is human.

Embodiment 54. A method of treating a suspected opioid overdose in a subject, the method comprising co-administering a sequestration agent with a central nervous system (CNS) active agent, wherein the CNS active agent is administered less than 5 minutes after the sequestration agent.

Embodiment 55. The method of embodiment 54, further comprising administration of an CNS active agent.

Embodiment 56. The method of any one of embodiments 54-55, wherein the sequestration agent or a pharmaceutically acceptable salt thereof is administered at about 10 mg/kg to 300 mg/kg.

Embodiment 57. The method of any one of embodiments 54-56, wherein CNS active agent or a pharmaceutically acceptable salt thereof is administered at about 100-400 μg/kg.

Embodiment 58. The method of any one of embodiments 54-57, wherein the sequestration agent comprises Compound A, or any derivative thereof.

Embodiment 59. The method of any one of embodiments 54-58, wherein the CNS active agent comprises naloxone or a pharmaceutically acceptable salt thereof.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating intoxication, overdose, or a symptom thereof due to at least one opioid in a human subject, the method comprising administering a therapeutically effective amount of:

i) a sequestration agent or a pharmaceutically acceptable salt thereof in an amount sufficient to sequester the at least one opioid, wherein the sequestration agent is an acyclic cucurbituril; and ii) an opioid receptor antagonist or a pharmaceutically acceptable salt thereof;

wherein the sequestration agent and the opioid receptor antagonist are administered simultaneously, or wherein the sequestration agent and opioid receptor antagonist are administered sequentially, wherein the opioid receptor antagonist is administered first.

2. The method of claim 1, wherein the sequestration agent and the opioid receptor antagonist are administered in one pharmaceutical composition.

3. The method of claim 2, wherein the pharmaceutical composition is a liquid dosage form.

4. The method of claim 2, wherein the pharmaceutical composition is in a form suitable for oral, intravenous, intramuscular, subcutaneous, intramedullary, intrathecal, intraperitoneal, intranasal, ophthalmic, pulmonary, transmucosal, transdermal, or topical administration.

5. The method of claim 1, wherein the sequestration agent and opioid receptor antagonist are administered in different pharmaceutical compositions.

6. The method of claim 1, wherein the sequestration agent and opioid receptor antagonist are administered simultaneously.

7. The method of claim 1, wherein the sequestration agent and opioid receptor antagonist are administered sequentially, wherein the opioid receptor antagonist is administered first.

8. The method of claim 7, wherein the sequestration agent is administered less than 5 minutes after the opioid receptor antagonist.

9. The method of claim 1, wherein the sequestration agent is Compound A, or a pharmaceutically acceptable salt thereof

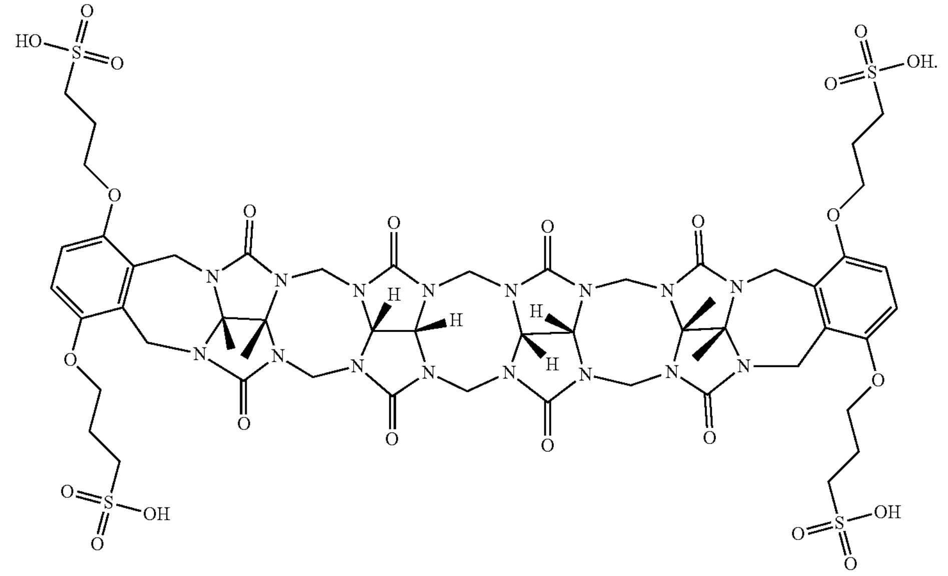

10. The method of claim 1, wherein the opioid receptor antagonist is a mu opioid receptor antagonist.

11. The method of claim 1, wherein the opioid receptor antagonist is selected form the group consisting of naloxone, pentazocine, nalbuphine, diprenorphine, methylnaltrexone, naloxegol, alvimopan, naltrexone, nalmefene, buprenorphine, and pharmaceutically acceptable salts thereof.

12. The method of claim 11, wherein the opioid antagonist is naloxone or a pharmaceutically acceptable salt thereof.

13. The method of claim 12, wherein the naloxone or pharmaceutically acceptable salt thereof is administered in a pharmaceutical composition, the pharmaceutical composition comprising from about 0.01% by weight to about 20% by weight of the naloxone or pharmaceutically acceptable salt thereof.

14. The method of claim 1, wherein i) the sequestration agent is Compound A, or a pharmaceutically acceptable salt thereof Compound A

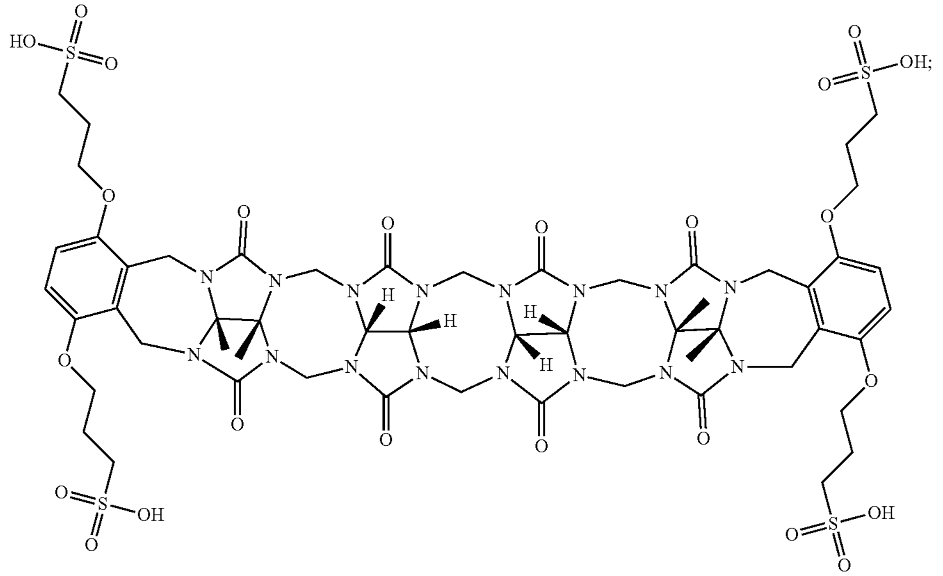

and ii) the opioid antagonist is naloxone or a pharmaceutically acceptable salt thereof.

15. The method of claim 1, wherein the opioid is selected a group consisting of fentanyl, fentanyl analogs, carfentanil, sufentanil, acetylfentanyl, alfentanil, heroin, morphine, oxycodone, codeine, hydrocodone, oxymorphone, and any pharmaceutically acceptable salts, and any combinations thereof.

16. The method of claim 15, wherein the sequestration agent binds to the opioid with a $K_a$ of at least $1\times10^3$ $M^{-1}$.

17. The method of claim 1, wherein the opioid receptor antagonist binds to the opioid with a $K_a$ of at least $1\times10^3$ $M^{-1}$.

18. The method of claim 1, wherein the sequestration agent binds to the opioid receptor antagonist with a $K_a$ of at least $1\times10^3$ $M^{-1}$.

19. The method of claim 1, wherein Compound A or a pharmaceutically acceptable salt thereof is administered at about 1 mg/kg to about 2,000 mg/kg.

20. The method of claim 1, wherein the opioid receptor antagonist is naloxone or a pharmaceutically acceptable salt thereof, wherein the naloxone or pharmaceutically acceptable salt thereof is administered at about 0.1 μg/kg to about 1,000 μg/kg.

21. The method of claim 1, wherein the administration is orally, intravenously, intramuscularly, subcutaneously, intramedullary, intrathecally, intraperitoneally, intranasal, ophthalmic, pulmonary, transmucosal, transdermal, or topically.

22. The method of claim 1, further comprising monitoring the human subject to determine whether a subsequent administration of an opioid antagonist is needed.

23. The method of claim 22, wherein the monitoring comprises measuring the human subject for abnormal heartrate, respiratory rate, appetite, cognitive capacity, or any combination thereof.

24. The method of claim 1, wherein treating intoxication, overdose, or a symptom thereof in said human subject comprises alleviating opioid intoxication or overdose in said human subject.

25. The method of claim 24, wherein said alleviating comprises restoration of normal respiration rate, wherein said normal respiration rate comprises at 12 to 20 breaths per minute.

26. The method of claim 24, wherein said alleviating comprises restoration of appetite.

27. The method of claim 24, wherein said alleviating comprises preventing opioid renarcotization.

28. The method of claim 1, further comprising at least a second administration of said opioid receptor antagonist.

29. The method of claim 28, wherein the at least second administration of said opioid receptor antagonist comprises at least 1, 2, 3, or 4 dose over 8 hours.

30. The method of claim 1, wherein administering said opioid receptor antagonist comprises administering at least 0.4 mg over 8 hours.

* * * * *